United States Patent
Iwazawa et al.

(10) Patent No.: US 10,335,514 B2
(45) Date of Patent: Jul. 2, 2019

(54) COMPOSITION, CELL STRUCTURE, PANCREATIC ISLET TRANSPLANTATION KIT, PANCREATIC ISLET CELL TRANSPLANTATION TREATMENT AGENT AND HYPOGLYCEMIC AGENT, COMPOSITION CONTAINING PANCREATIC ISLET, KIT CONTAINING PANCREATIC ISLET, AND PANCREATIC ISLET TRANSPLANTATION TREATMENT AGENT AND HYPOGLYCEMIC AGENT

(71) Applicant: FUJIFILM Corporation, Tokyo (JP)

(72) Inventors: Reiko Iwazawa, Ashigarakami-gun (JP); Kentaro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 100 days.

(21) Appl. No.: 15/472,855

(22) Filed: Mar. 29, 2017

(65) Prior Publication Data
US 2017/0203005 A1 Jul. 20, 2017

Related U.S. Application Data

(63) Continuation of application No. PCT/JP2015/077516, filed on Sep. 29, 2015.

(30) Foreign Application Priority Data

Sep. 30, 2014 (JP) .................. 2014-200220
Dec. 25, 2014 (JP) .................. 2014-262637
Dec. 25, 2014 (JP) .................. 2014-262662
Feb. 19, 2015 (JP) .................. 2015-030398

(51) Int. Cl.
| | | |
|---|---|---|
| A61L 27/38 | (2006.01) | |
| A61K 9/16 | (2006.01) | |
| A61K 35/39 | (2015.01) | |
| A61K 47/42 | (2017.01) | |
| A61L 27/00 | (2006.01) | |
| A61K 35/12 | (2015.01) | |
| A61L 27/22 | (2006.01) | |
| A61L 27/56 | (2006.01) | |

(52) U.S. Cl.
CPC ............ *A61L 27/3804* (2013.01); *A61K 9/16* (2013.01); *A61K 35/12* (2013.01); *A61K 35/39* (2013.01); *A61K 47/42* (2013.01); *A61L 27/00* (2013.01); *A61L 27/222* (2013.01); *A61L 27/3886* (2013.01); *A61L 27/56* (2013.01); *A61L 2300/64* (2013.01); *A61L 2430/22* (2013.01)

(58) Field of Classification Search
None
See application file for complete search history.

(56) References Cited

U.S. PATENT DOCUMENTS

2013/0071441 A1 3/2013 Iwazawa et al.
2013/0171114 A1 7/2013 Tanemura et al.

FOREIGN PATENT DOCUMENTS

| EP | 2 601 996 A1 | 6/2013 |
| JP | 2014-012114 A | 1/2014 |
| WO | 2011/108517 A1 | 9/2011 |
| WO | 2012/018127 A1 | 2/2012 |

OTHER PUBLICATIONS

International Preliminary Report on Patentability mailed from the International Bureau in counterpart International Application No. PCT/JP2015/077516, dated Apr. 13, 2017.
Goichi Yanai, et al., "Electrofusion of Mesenchymal Stem Cells and Islet Cells for Diabetes Therapy: A Rat Model", PLOS ONE, vol. 8, No. 5, May 2013, pp. 1-10, e64499.
Taihei Ito, et al., "Mesenchymal Stem Cell and Islet Co-Transplantation Promotes Graft Revascularization and Function", Transplantation, vol. 89, No. 12, Jun. 27, 2010, pp. 1438-1445.
M. K. Ju, et al., "Proliferation and Functional Assessment of Pseudo-islets With the Use of Pancreatic Endocrine Cells", Transplantation Proceedings, vol. 45, No. 5, 2013, pp. 1885-1888.
Tasneem Bhaiji, et al., "Improving cellular function and immune protection via layer-by-layer nanocoating of pancreatic islet β-cell spherolds cocultured with mesenchymal stem cells", Journal of Biomedical Materials Research, vol. 100A, No. 6, pp. 1628-1636, 2012.
International Search Report for PCT/JP2015/077516 dated Dec. 15, 2015 [PCT/ISA/210].
Office Action dated Jan. 16, 2018, from the Japanese Patent Office in counterpart Japanese Application No. 2016-552062.
Yanai, G., et al., "Electrofusion of Mesenchymal Stem Cells and Islet Cells for Diabetes Therapy: A Rat Model", PLOS ONE, 2013, vol. 8, Issue 5, pp. 2-11/E (10 pages).

(Continued)

*Primary Examiner* — Michelle F. Paguio Frising
(74) *Attorney, Agent, or Firm* — Sughrue Mion, PLLC

(57) ABSTRACT

An object is to provide a composition containing a pancreatic islet, a cell structure containing a pancreatic islet or a pancreatic islet cell, a pancreatic islet transplantation kit, a pancreatic islet transplantation treatment agent, and a hypoglycemic agent which improve at least one of glucose sensitivity or blood sugar level-reducing performance after transplantation, and to provide a composition containing a pancreatic islet, a kit containing a pancreatic islet, a pancreatic islet cell transplantation treatment agent, and a hypoglycemic agent which can improve glucose sensitivity. A composition including (A): a cell structure containing a biocompatible macromolecular block and at least one kind of cell and in which a plurality of the above-described macromolecular blocks are arranged in gaps between a plurality of the above-described cells; and (B): a pancreatic islet, and a composition containing a pancreatic islet; and a spheroid formed of at least one type of stem cell are provided.

9 Claims, 5 Drawing Sheets

Specification includes a Sequence Listing.

(56) References Cited

OTHER PUBLICATIONS

Extended European Search Report dated Oct. 20, 2017 from the European Patent Office in counterpart European Application No. 15846323.2.
Partial supplementary European search report dated Jul. 3, 2017, from the European Patent Office in counterpart European Application No. 15846323.2.
Bretzel, R.G., et al., "Pancreatic islet and stem cell transplantation: new strategies in cell therapy of diabetes mellitus", Panminerva Medica, vol. 46, No. 1, 2004, XP009194526, pp. 25-42 (18 pages).

(2) PANCREATIC ISLETS AND CELL AGGREGATIONS (COMPARATIVE EXAMPLE)

(3) PANCREATIC ISLETS AND CELL STRUCTURES (PRESENT INVENTION)

(7) AGGREGATION OF PANCREATIC ISLETS AND CELL STRUCTURES (PRESENT INVENTION)

SEQUENCE LISTING

<160> NUMBER OF SEQ ID NOS: 11

<210> SEQ ID NO 1

```
<211> LENGTH: 571
<212> TYPE: PRT
<213> ORGANISM: Artificial Sequence
<220> FEATURE:
<223> OTHER INFORMATION: Synthetic peptide sequence

<400> SEQUENCE: 1
```

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270

Asp Gly Val Arg Gly Leu Ala Gly Pro Ile Gly Pro Pro Gly Glu Arg
        275                 280                 285

Gly Ala Ala Gly Leu Pro Gly Pro Lys Gly Glu Arg Gly Asp Ala Gly
    290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
        355                 360                 365

Pro Gly Lys Asp Gly Val Arg Gly Leu Ala Gly Pro Pro Gly Ala Pro
    370                 375                 380

```
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
            405                 410                 415
Lys Gly Ala Asp Gly Ala Pro Gly Ala Pro Gly Leu Gln Gly Met Pro
        420                 425                 430
Gly Glu Arg Gly Ala Ala Gly Leu Pro Gly Pro Lys Gly Glu Arg Gly
    435                 440                 445
Asp Ala Gly Pro Lys Gly Ala Asp Gly Ala Pro Gly Lys Asp Gly Val
450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
            485                 490                 495
Ala Asp Gly Ala Pro Gly Lys Asp Gly Val Arg Gly Leu Ala Gly Pro
        500                 505                 510
Ile Gly Pro Pro Gly Pro Ala Gly Ala Pro Gly Ala Pro Gly Leu Gln
    515                 520                 525
Gly Met Pro Gly Glu Arg Gly Ala Ala Gly Leu Pro Gly Pro Lys Gly
530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 4

Pro Asp Ser Gly Arg
1               5

<210> SEQ ID NO 5
<211> LENGTH: 7
```

```
<212> TYPE: PRT
<213> ORGANISM: Artificial Sequence
<220> FEATURE:
<223> OTHER INFORMATION: Synthetic peptide sequence

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 10

Glu Arg Gly Asp
1

<210> SEQ ID NO 11
<211> LENGTH: 571
<212> TYPE: PRT
```

<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (1)..(571)
<223> OTHER INFORMATION: all Xaa is independently any amino acid

<400> SEQUENCE: 11

```
Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa Gly Xaa Xaa Gly Xaa Xaa Gly Xaa Xaa Gly Xaa Xaa Gly Xaa Xaa
        35                  40                  45

Gly Xaa Xaa Gly Xaa Xaa Gly Xaa Xaa Gly Xaa Xaa Gly Xaa Xaa Gly
50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
        85                  90                  95

Gly Xaa Xaa Gly Xaa Xaa Gly Xaa Xaa Gly Xaa Xaa Gly Xaa Xaa Gly
            100                 105                 110

Xaa Xaa Gly Xaa Xaa Gly Xaa Xaa Gly Xaa Xaa Gly Xaa Xaa Gly Xaa
            115                 120                 125

Xaa Gly Xaa Xaa Gly Xaa Xaa Gly Xaa Xaa Gly Xaa Xaa Gly Xaa Xaa
            130                 135                 140

Gly Xaa Xaa Gly Xaa Xaa Gly Xaa Xaa Gly Xaa Xaa Gly Xaa Xaa Gly
145                 150                 155                 160

Xaa Xaa Gly Xaa Xaa Gly Xaa Xaa Gly Xaa Xaa Gly Xaa Xaa Gly Xaa
                165                 170                 175

Xaa Gly Xaa Xaa Gly Xaa Xaa Gly Xaa Xaa Gly Xaa Xaa Gly Xaa Xaa
            180                 185                 190

Gly Xaa Xaa Gly Xaa Xaa Gly Xaa Xaa Gly Xaa Xaa Gly Xaa Xaa Gly
        195                 200                 205

Xaa Xaa Gly Xaa Xaa Gly Xaa Xaa Gly Xaa Xaa Gly Xaa Xaa Gly Xaa
    210                 215                 220

Xaa Gly Xaa Xaa Gly Xaa Xaa Gly Xaa Xaa Gly Xaa Xaa Gly Xaa Xaa
225                 230                 235                 240

Gly Xaa Xaa Gly Xaa Xaa Gly Xaa Xaa Gly Xaa Xaa Gly Xaa Xaa Gly
                245                 250                 255

Xaa Xaa Gly Xaa Xaa Gly Xaa Xaa Gly Xaa Xaa Gly Xaa Xaa Gly Xaa
            260                 265                 270

Xaa Gly Xaa Xaa Gly Xaa Xaa Gly Xaa Xaa Gly Xaa Xaa Gly Xaa Xaa
            275                 280                 285

Gly Xaa Xaa Gly Xaa Xaa Gly Xaa Xaa Gly Xaa Xaa Gly Xaa Xaa Gly
        290                 295                 300

Xaa Xaa Gly Xaa Xaa Gly Xaa Xaa Gly Xaa Xaa Gly Xaa Xaa Gly Xaa
305                 310                 315                 320

Xaa Gly Xaa Xaa Gly Xaa Xaa Gly Xaa Xaa Gly Xaa Xaa Gly Xaa Xaa
                325                 330                 335

Gly Xaa Xaa Gly Xaa Xaa Gly Xaa Xaa Gly Xaa Xaa Gly Xaa Xaa Gly
            340                 345                 350

Xaa Xaa Gly Xaa Xaa Gly Xaa Xaa Gly Xaa Xaa Gly Xaa Xaa Gly Xaa
            355                 360                 365
```

-continued

```
Xaa Gly Xaa Xaa Gly Xaa Xaa Gly Xaa Xaa Gly Xaa Xaa Gly Xaa Xaa
        370                 375                 380
Gly Xaa Xaa Gly Xaa Xaa Gly Xaa Xaa Gly Xaa Xaa Gly Xaa Xaa Gly
385                 390                 395                 400
Xaa Xaa Gly Xaa Xaa Gly Xaa Xaa Gly Xaa Xaa Gly Xaa Xaa Gly Xaa
                405                 410                 415
Xaa Gly Xaa Xaa Gly Xaa Xaa Gly Xaa Xaa Gly Xaa Xaa Gly Xaa Xaa
        420                 425                 430
Gly Xaa Xaa Gly Xaa Xaa Gly Xaa Xaa Gly Xaa Xaa Gly Xaa Xaa Gly
            435                 440                 445
Xaa Xaa Gly Xaa Xaa Gly Xaa Xaa Gly Xaa Xaa Gly Xaa Xaa Gly Xaa
        450                 455                 460
Xaa Gly Xaa Xaa Gly Xaa Xaa Gly Xaa Xaa Gly Xaa Xaa Gly Xaa Xaa
465                 470                 475                 480
Gly Xaa Xaa Gly Xaa Xaa Gly Xaa Xaa Gly Xaa Xaa Gly Xaa Xaa Gly
                485                 490                 495
Xaa Xaa Gly Xaa Xaa Gly Xaa Xaa Gly Xaa Xaa Gly Xaa Xaa Gly Xaa
            500                 505                 510
Xaa Gly Xaa Xaa Gly Xaa Xaa Gly Xaa Xaa Gly Xaa Xaa Gly Xaa Xaa
        515                 520                 525
Gly Xaa Xaa Gly Xaa Xaa Gly Xaa Xaa Gly Xaa Xaa Gly Xaa Xaa Gly
        530                 535                 540
Xaa Xaa Gly Xaa Xaa Gly Xaa Xaa Gly Xaa Xaa Gly Xaa Xaa Gly Xaa
545                 550                 555                 560
Xaa Gly Xaa Xaa Gly Xaa Xaa Gly Xaa Xaa Gly
            565                 570
```

COMPOSITION, CELL STRUCTURE, PANCREATIC ISLET TRANSPLANTATION KIT, PANCREATIC ISLET CELL TRANSPLANTATION TREATMENT AGENT AND HYPOGLYCEMIC AGENT, COMPOSITION CONTAINING PANCREATIC ISLET, KIT CONTAINING PANCREATIC ISLET, AND PANCREATIC ISLET TRANSPLANTATION TREATMENT AGENT AND HYPOGLYCEMIC AGENT

CROSS-REFERENCE TO RELATED APPLICATIONS

The present application is a continuation of PCT/JP2015/77516 filed on Sep. 29, 2015 and claims priority under 35 U.S.C. § 119 of Japanese Patent Applications No. 200220/2014 filed on Sep. 30, 2014, No. 262637/2014 filed on Dec. 25, 2014, No. 262662/2014 filed on Dec. 25, 2014, and No. 30398/2015 filed on Feb. 19, 2015.

BACKGROUND OF THE INVENTION

1. Field of the Invention

The present invention relates to a composition containing a pancreatic islet, a cell structure containing a pancreatic islet or a pancreatic islet cell, a pancreatic islet transplantation kit, a pancreatic islet cell transplantation treatment agent, and a hypoglycemic agent. The present invention further relates to a composition containing a pancreatic islet, a kit containing a pancreatic islet, a pancreatic islet transplantation treatment agent, and a hypoglycemic agent.

2. Description of the Related Art

Currently, regenerative medicine, which regenerates living body tissues and organs having functional disorders or dysfunction, is put into practical use. The regenerative medicine is new medical technology creating a form or a function of a living body tissue that cannot be recovered with only natural healing ability possessed by a living body, which is the same as that of an original tissue, again, using three factors including a cell, a scaffold, and a growth factor. In recent years, treatment using cells is gradually realized. Examples thereof include cartilage treatment using autologous chondrocytes, and cultured epidermis using autologous cells; bone regeneration treatment using mesenchymal stem cells; myocardial cell sheet treatment using myoblasts; cornea regeneration treatment using corneal epithelial sheets; and nerve regeneration treatment.

A cell structure, which contains cells and macromolecular blocks having biocompatibility, and in which the plurality of the above-described macromolecular blocks are arranged in gaps between the plurality of the above-described cells, is disclosed in WO2011/108517A. In the cell structure disclosed in WO2011/108517A, it is possible to deliver nutrients to the inside of the cell structure from the outside. The cell structure has a sufficient thickness, and cells exist in the structure uniformly. In Example of WO2011/108517A, high cell survival activity is verified using a macromolecular block formed of a recombinant gelatin material or a natural gelatin material. A cell structure for cell transplantation, which contains a macromolecular block having biocompatibility and at least one kind of cell, and in which the plurality of the above-described macromolecular blocks are arranged in the gaps between the plurality of the above-described cells, is disclosed in JP2014-12114A. In Example of JP2014-12114A, angiogenesis is evaluated using the cell structure for cell transplantation.

It is necessary for severe diabetic patients among diabetic patients to receive an insulin injection throughout their life. A transplantation treatment of transplanting a pancreatic islet which produces insulin into the liver of a diabetic patient to permanently fix the pancreatic islet to the liver is performed as a treatment method for releasing diabetic patients from an insulin injection. It is considered that there are β cells, which secrete insulin, in the pancreatic islet in the pancreas, and therefore, it is possible to secrete insulin by transplanting the pancreatic islet.

Transplantation treatment called pancreatic islet transplantation is performed on a patient whose pancreas cannot secrete insulin itself. It is considered that there are β cells, which secrete insulin, in the pancreatic islet in the pancreas, and therefore, it is possible to secrete insulin by transplanting the pancreatic islet. Currently, pancreatic islet transplantation using the Edmonton Protocol method in which a pancreatic islet is injected into blood from the portal vein is performed as the method for transplanting a pancreatic islet.

It is shown in Yanai G et al. (2013) Electrofusion of Mesenchymal Stem Cells and Islet Cells for Diabetes Therapy: A Rat Model. PLOS ONE, Volume 8, Issue 5, e64499 that glucose sensitivity disappears after 10 days of culturing in a case of using only a pancreatic islet in an in vitro glucose sensitivity test, but glucose sensitivity is maintained even after 10 days of culturing in a case of using pancreatic islet cells and mesenchymal stem cells which have been dispersed and in a case of using a fused body of pancreatic islet cells and mesenchymal stem cells (page 5, right column, lines 4 to 6, FIG. 5-b). In addition, in Yanai G et al. (2013) Electrofusion of Mesenchymal Stem Cells and Islet Cells for Diabetes Therapy: A Rat Model. PLOS ONE, Volume 8, Issue 5, e64499, the blood sugar level in vivo in a case of using only a pancreatic islet (Group 3) is the same as that in a case where a pancreatic islet and a mesenchymal stem cell is cultured together (Group 6) (FIG. 8a). It is shown in Ito T et al. (2010) Mesenchymal stem Cell and Islet Co-Transplantation Promotes Graft Revascularization and Function. Transplantation, Volume 89, Number 12, 1438-1445 that the blood sugar level is decreased by a transplanting mesenchymal stem cell and a pancreatic islet together whereas the blood sugar level is not decreased in a case where only a pancreatic islet is transplanted in vivo.

SUMMARY OF THE INVENTION

Currently, pancreatic islet transplantation using the Edmonton Protocol method in which a pancreatic islet is injected into blood from the portal vein is performed as a method for transplanting a pancreatic islet. However, there is a problem in that the proportion of insulin left after the transplantation is decreased. One of the causes is that, for example, it is impossible to maintain cell activities (glucose sensitivity) of the pancreatic islet after the transplantation. It is considered that it is possible to reduce the blood sugar level after the transplantation if it is possible to maintain glucose sensitivity of pancreatic islet cells, and therefore, it is possible to increase the proportion of insulin left after the transplantation.

In WO2011/108517A and JP2014-12114A, there is neither a disclosure that a pancreatic islet is transplanted nor a disclosure that pancreatic islet cells and stem cells are combined to be made as a cell structure. In addition, in WO2011/108517A and JP2014-12114A, there is neither a disclosure of Example using a pancreatic islet cell or a pancreatic islet nor a disclosure relating to glucose sensitivity of pancreatic islet cells after transplantation. It is shown in Yanai G et al. (2013) Electrofusion of Mesenchymal Stem Cells and Islet Cells for Diabetes Therapy: A Rat Model. PLOS ONE, Volume 8, Issue 5, e64499 that the glucose sensitivity is maintained even after 10 days of culturing in a case of using pancreatic islet cells and mesenchymal stem cells which have been dispersed and in a case of using a fused body of pancreatic islet cells and mesenchymal stem cells, using an in vitro test. However, it is unclear whether the glucose sensitivity of a pancreatic islet after in vivo transplantation is sufficiently exhibited or whether the blood sugar level is sufficiently decreased. It is shown in Ito T et al. (2010) Mesenchymal stem Cell and Islet Co-Transplantation Promotes Graft Revascularization and Function. Transplantation, Volume 89, Number 12, 1438-1445 that the blood sugar level is decreased by transplanting pancreatic islets and mesenchymal stem cells. However, a method for further improving the glucose sensitivity of a pancreatic islet is required in order to reduce the number of pancreatic islets to be transplanted.

As described above, development of a technique for further improving the glucose sensitivity of a pancreatic islet after transplantation or a technique for reducing the blood sugar level is required. An object of the present invention is to provide a composition containing a pancreatic islet, a cell structure containing a pancreatic islet or a pancreatic islet cell, and a pancreatic islet transplantation kit in which at least one of glucose sensitivity or blood sugar level-reducing performance after transplantation is improved. Another object of the present invention is to provide a pancreatic islet cell transplantation treatment agent and a hypoglycemic agent which contain the above-described composition, the above-described cell structure, or the pancreatic islet transplantation kit. A still another object of the present invention is to provide a composition containing a pancreatic islet and a kit containing a pancreatic islet which can improve the glucose sensitivity. A still another object of the present invention is to provide a pancreatic islet cell transplantation treatment agent and a hypoglycemic agent which contain the above-described composition or the above-described kit.

The present inventors have conducted extensive studies in order to solve the above-described problems. As a result, it has been shown that glucose sensitivity is improved by mixing a macromolecular block with a pancreatic islet or a pancreatic islet cell and culturing the mixture, compared to a case where a macromolecular block is not used. In addition, it has become clear that the amount of insulin produced in a pancreatic islet is improved in a case where a mixture of a pancreatic islet and a macromolecular block is transplanted into a diabetic mouse, and therefore, it is possible to reduce the blood sugar level. The present inventors have further conducted extensive studies in order to solve the above-described problems. As a result, it has been shown that the glucose sensitivity of a pancreatic islet after transplantation is improved using a composition containing a pancreatic islet and a spheroid of a stem cell such as a mesenchymal stem cell, compared to a case of using a composition containing a pancreatic islet and a dispersed stem cell. The present invention has been completed based on these findings.

That is, according to the present invention, the following inventions are provided.
(1) A composition comprising: A: a cell structure which contains a biocompatible macromolecular block and at least one kind of cell and in which a plurality of the above-described macromolecular blocks are arranged in gaps between a plurality of the above-described cells; and B: a pancreatic islet.
(2) The composition according to (1), in which the above-described pancreatic islet is an aggregate of an α cell, a β cell, a δ cell, an ε cell, and a PP cell.
(3) The composition according to (1) or (2), in which at least a mesenchymal stem cell is included as the above-described cell.
(4) The composition according to any one of (1) to (3), in which the above-described cell structure contains 0.0000001 μg to 1 μg of a biocompatible macromolecular block per cell.
(5) The composition treatment according to any one of (1) to (4), in which the size of one of the above-described biocompatible macromolecular blocks is 10 μm to 300 μm.
(6) The composition according to any one of (1) to (5), in which the thickness or the diameter of the above-described cell structure is 100 μm to 3 cm.
(7) The composition according to any one of (1) to (6), in which the above-described biocompatible macromolecular block is formed of a recombinant peptide.
(8) The composition according to (7), in which the above-described recombinant peptide is any of a peptide formed of an amino acid sequence described in SEQ ID No: 1; a peptide which is formed of an amino acid sequence in which one or a plurality of amino acids are deleted, substituted, or added in the amino acid sequence described in SEQ ID No: 1, and has biocompatibility; and a peptide which is formed of an amino acid sequence having 80% or more sequence identity to the amino acid sequence described in SEQ ID No: 1, and has biocompatibility.
(9) The composition according to any one of (1) to (8), in which, in the above-described biocompatible macromolecular block, the biocompatible macromolecules are cross-linked using heat, ultraviolet rays, or enzyme.
(10) The composition according to any one of (1) to (9), in which the above-described biocompatible macromolecular block is in a granular form obtained by pulverizing a porous body of a biocompatible macromolecule.
(11) A cell structure comprising: a biocompatible macromolecular block; at least one kind of cell; and a pancreatic islet, in which a plurality of the above-described macromolecular blocks are arranged in gaps between a plurality of the above-described cells.
(12) The cell structure according to (11), in which the above-described pancreatic islet is an aggregate of an α cell, a β cell, a δ cell, an ε cell, and a PP cell.
(13) The cell structure according to (11) or (12), in which at least a mesenchymal stem cell is included as the above-described cell.
(14) The cell structure according to any one of (11) to (13), in which 0.0000001 μg to 1 μg of a biocompatible macromolecular block per cell is included.
(15) A cell structure comprising: a biocompatible macromolecular block; and at least two kinds of cells, in which a plurality of the above-described macromolecular blocks are arranged in gaps between a plurality of the above-described cells, and at least pancreatic islet cells and stem cells are included as the above-described cells.
(16) The cell structure according to (15), in which the above-described pancreatic islet cells contain an α cell, a β cell, a δ cell, an ε cell, and a PP cell.
(17) The cell structure according to (15) or (16), in which at least a mesenchymal stem cell is included as the above-described stem cell.
(18) The cell structure according to any one of (15) to (17), in which 0.0000001 μg to 1 μg of a biocompatible macromolecular block per cell is included with respect to all cells containing the pancreatic islet cells and the stem cells.
(19) The cell structure according to any one of (15) to (18), in which 10% by number to 90% by number of pancreatic islet cells are included with respect to all the cells containing the pancreatic islet cells and the stem cells.
(20) The cell structure according to any one of (11) to (19), in which SI represented by the following equation is greater than or equal to 3.0.

SI=amount of insulin during culture in 20 mM glucose medium/amount of insulin during culture in 3 mM glucose medium

(21) The cell structure according to any one of (11) to (20), in which the size of one of the above-described biocompatible macromolecular blocks is 10 µm to 300 µm.
(22) The cell structure according to any one of (11) to (21), in which the thickness or the diameter of the above-described cell structure is 100 µm to 3 cm.
(23) The cell structure according to any one of (11) to (22), in which the above-described biocompatible macromolecular block is formed of a recombinant peptide.
(24) The cell structure according to (23), in which the recombinant peptide is any of a peptide which is formed of an amino acid sequence described in SEQ ID No: 1; a peptide which is formed of an amino acid sequence in which one or a plurality of amino acids are deleted, substituted, or added in the amino acid sequence described in SEQ ID No: 1, and has biocompatibility; and a peptide which is formed of an amino acid sequence having 80% or more sequence identity to the amino acid sequence described in SEQ ID No: 1, and has biocompatibility.
(25) The cell structure according to any one of (11) to (24), in which, in the above-described biocompatible macromolecular block, the above-described biocompatible macromolecules are cross-linked using heat, ultraviolet rays, or enzyme.
(26) The cell structure according to any one of (11) to (25), in which the above-described biocompatible macromolecular block is in a granular form obtained by pulverizing a porous body of a biocompatible macromolecule.
(27) A pancreatic islet transplantation kit, comprising: A: a cell structure which contains a biocompatible macromolecular block and at least one kind of cell and in which a plurality of the above-described macromolecular blocks are arranged in gaps between a plurality of the above-described cells; and B: a pancreatic islet.
(28) The pancreatic islet transplantation kit according to (27), in which the above-described pancreatic islet is an aggregate of an α cell, a β cell, a δ cell, an ε cell, and a PP cell.
(29) The pancreatic islet transplantation kit according to (27) or (28), in which the above-described cells contain mesenchymal stem cells.
(30) The pancreatic islet transplantation kit according to any one of (27) to (29), in which the above-described cell structure contains 0.0000001 µg to 1 µg of a biocompatible macromolecular block per cell.
(31) The pancreatic islet transplantation kit according to any one of (27) to (30), in which the size of one of the above-described biocompatible macromolecular blocks is 10 µm to 300 µm.
(32) The pancreatic islet transplantation kit according to any one of (27) to (31), in which the thickness or the diameter of the above-described cell structure is 100 µm to 3 cm.
(33) The pancreatic islet transplantation kit according to any one of (27) to (32), in which the above-described biocompatible macromolecular block is formed of a recombinant peptide.
(34) The pancreatic islet transplantation kit according to (33), in which the above-described recombinant peptide is any of a peptide which is formed of an amino acid sequence described in SEQ ID No: 1; a peptide which is formed of an amino acid sequence in which one or a plurality of amino acids are deleted, substituted, or added in the amino acid sequence described in SEQ ID No: 1, and has biocompatibility; and a peptide which is formed of an amino acid sequence having 80% or more sequence identity to the amino acid sequence described in SEQ ID No: 1, and has biocompatibility.
(35) The pancreatic islet transplantation kit according to any one of (27) to (34), in which, in the above-described biocompatible macromolecular block, the above-described biocompatible macromolecules are cross-linked using heat, ultraviolet rays, or enzyme.
(36) The pancreatic islet transplantation kit according to any one of (27) to (35), in which the above-described biocompatible macromolecular block is in a granular form obtained by pulverizing a porous body of a biocompatible macromolecule.
(37) A pancreatic islet cell transplantation treatment agent, comprising: the composition according to any one of (1) to (10); the cell structure according to any one of (11) to (26); or the pancreatic islet transplantation kit according to any one of (27) to (36).
(38) The pancreatic islet cell transplantation treatment agent according to (37), in which an administration site is under the skin or within the muscle.
(39) A hypoglycemic agent comprising: the composition according to any one of (1) to (10); the cell structure according to any one of (11) to (26); or the pancreatic islet transplantation kit according to any one of (27) to (36).
(40) The hypoglycemic agent according to (39), in which an administration site is under the skin or within the muscle.

Furthermore, according to the present invention, the following inventions are provided.

(41) A cell transplantation method comprising: a step of transplanting the composition according to any one of (1) to (10); the cell structure according to any one of (11) to (26); or the pancreatic islet transplantation kit according to any one of (27) to (36), into a patient who requires transplantation of a pancreatic islet or a pancreatic islet cell.
(42) A blood sugar reduction method, comprising: a step of transplanting the composition according to any one of (1) to (10); the cell structure according to any one of (11) to (26); or the pancreatic islet transplantation kit according to any one of (27) to (36), into a patient who requires reduction in blood sugar.
(43) The composition according to any one of (1) to (10) which is used for pancreatic islet cell transplantation treatment.
(44) The cell structure according to any one of (11) to (26) which is used for pancreatic islet cell transplantation treatment.
(45) The pancreatic islet transplantation kit according to any one of (27) to (36) which is used for pancreatic islet cell transplantation treatment.
(46) The composition according to any one of (1) to (10) which is used for blood sugar reduction treatment.
(47) The cell structure according to any one of (11) to (26) which is used for blood sugar reduction treatment.

(48) The pancreatic islet transplantation kit according to any one of (27) to (36) which is used for blood sugar reduction treatment.
(49) Use of the composition according to any one of (1) to (10); the cell structure according to any one of (11) to (26); or the pancreatic islet transplantation kit according to any one of (27) to (36), for producing a pancreatic islet cell transplantation treatment agent.
(50) Use of the composition according to any one of (1) to (10); the cell structure according to any one of (11) to (26); or the pancreatic islet transplantation kit according to any one of (27) to (36), for producing a hypoglycemic agent.

Furthermore, according to the present invention, the following inventions are provided.

(51) A composition comprising: a pancreatic islet; and a spheroid formed of at least one type of stem cell.
(52) The composition according to (51), in which at least a somatic stem cell is included as the above-described stem cell.
(53) The composition according to (51) or (52), in which at least a mesenchymal stem cell is included as the above-described stem cell.
(54) The composition according to any one of (51) to (53), in which spheroid is formed of one type of stem cell.
(55) The composition according to any one of (51) to (54), in which the above-described pancreatic islet is an aggregate of an α cell, a β cell, a δ cell, an ε cell, and a PP cell.
(56) The composition according to any one of (51) to (55), in which the above-described spheroid has a spherical shape with a diameter of 100 μm to 500 μm.
(57) The composition according to any one of (51) to (56), in which a plurality of the above-described pancreatic islets and a plurality of the above-described spheroids are included in a liquid medium.
(58) The composition according to any one of (51) to (57), in which the above-described plurality of pancreatic islets and the above-described plurality of spheroids form a cell aggregation in the liquid medium.
(59) The composition according to any one of (51) to (57), in which the above-described plurality of pancreatic islets and the above-described plurality of spheroids float in the liquid medium.
(60) The composition according to any one of (51) to (59), in which SI represented by the following equation is greater than or equal to 1.7.

SI=amount of insulin during culture in 20 mmol/L glucose medium/amount of insulin during culture in 3 mmol/L glucose medium

(61) The composition according to any one of (51) to (60) which is used for transplanting a pancreatic islet into a living body.
(62) A kit comprising: a pancreatic islet; and a spheroid formed of at least one type of stem cell.
(63) The kit according to (62), in which at least a somatic stem cell is included as the above-described stem cell.
(64) The kit according to (62) or (63), in which at least a mesenchymal stem cell is included as the above-described stem cell.
(65) The kit according to any one of (62) to (64), in which spheroid is formed of one type of stem cell.
(66) The kit according to any one of (62) to (65), in which the above-described pancreatic islet is an aggregate of an α cell, a β cell, a δ cell, an ε cell, and a PP cell.
(67) The kit according to any one of (62) to (66), in which the above-described spheroid has a spherical shape with a diameter of 100 μm to 500 μm.
(68) The kit according to any one of (62) to (67) which is used for transplanting a pancreatic islet into a living body.
(69) A pancreatic islet transplantation treatment agent, comprising: the composition according to any one of (51) to (61); or the kit according to any one of (62) to (68).
(70) The pancreatic islet transplantation treatment agent according to (69), in which an administration site is under the skin or within the muscle.
(71) A hypoglycemic agent comprising: the composition according to any one of (51) to (61); or the kit according to any one of (62) to (68).
(72) The hypoglycemic agent according to (71), in which an administration site is under the skin or within the muscle.

Furthermore, according to the present invention, the following inventions are provided.

(73) A pancreatic islet transplantation method comprising: a step of transplanting the composition according to any one of (51) to (61); or the kit according to any one of (62) to (68), into a patient who requires transplantation of a pancreatic islet.
(74) A blood sugar reduction method, comprising: a step of transplanting the composition according to any one of (51) to (61); or the kit according to any one of (62) to (68), into a patient who requires reduction in blood sugar.
(75) The composition according to any one of (51) to (61) which is used for pancreatic islet transplantation treatment.
(76) The kit according to any one of (62) to (68) which is used for pancreatic islet transplantation treatment.
(77) The composition according to any one of (51) to (61) which is used for blood sugar reduction treatment.
(78) The kit according to any one of (62) to (68) which is used for blood sugar reduction treatment.
(79) Use of the composition according to any one of (51) to (61) or the kit according to any one of (62) to (68), for producing a pancreatic islet transplantation treatment agent.
(80) Use of the composition according to any one of (51) to (61) or the kit according to any one of (62) to (68), for producing hypoglycemic agent.

According to a composition containing a pancreatic islet, a cell structure containing a pancreatic islet or a pancreatic islet cell, a pancreatic islet transplantation kit, a pancreatic islet cell transplantation treatment agent, and a hypoglycemic agent of the present invention, it is possible to improve at least one of glucose sensitivity or blood sugar level-reducing performance after transplantation.

According to a composition containing a pancreatic islet, a kit containing a pancreatic islet, a pancreatic islet transplantation treatment agent, and a hypoglycemic agent of the present invention, it is possible to improve the glucose sensitivity and to reduce the blood sugar level.

DESCRIPTION OF THE PREFERRED EMBODIMENTS

Figure 1:
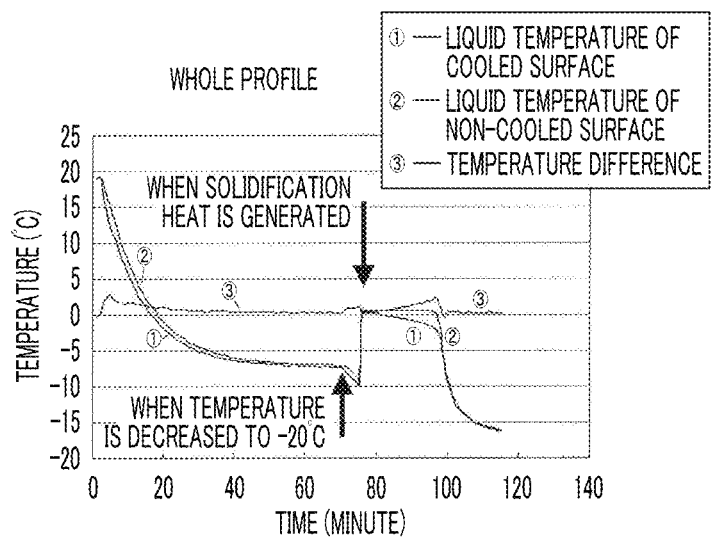
FIG. 1 shows a temperature profile when freezing a solvent in Examples.

Hereinafter, an embodiment of the present invention will be described in detail.

A first aspect of the present invention is an aspect described in the above-described (1) to (50). First, the first aspect of the present invention will be described.

[Composition, Cell Structure, and Pancreatic Islet Transplantation Kit]

A composition of the present invention is a composition including: A: a cell structure which contains a biocompatible macromolecular block and at least one kind of cell and in which a plurality of the macromolecular blocks are arranged in gaps between a plurality of the cells; and B: a pancreatic islet.

A cell structure of the present invention is a cell structure including a biocompatible macromolecular block, at least one kind of cell, and a pancreatic islet, in which a plurality of the above-described macromolecular blocks are arranged in gaps between a plurality of the above-described cells; or a cell structure including a biocompatible macromolecular block, and at least two kinds of cells, in which a plurality of the above-described macromolecular blocks are arranged in gaps between a plurality of the above-described cells, and the cell structure contains at least pancreatic islet cells and stem cells as the above-described cells.

In some cases, the cell structure of the present invention is called a mosaic cell aggregation (a cell aggregation in a mosaic shape) in the present specification.

A pancreatic islet transplantation kit of the present invention is a pancreatic islet transplantation kit including: A: a cell structure which contains a biocompatible macromolecular block and at least one kind of cell and in which a plurality of the above-described macromolecular blocks are arranged in gaps between a plurality of the above-described cells; and B: a pancreatic islet.

The composition called in the present invention is a composition including a cell structure and a pancreatic islet and means an arbitrary mixture including a cell structure and a pancreatic islet. The composition of the present invention may be any one of (i) a case where a pancreatic islet forms a cell structure by being included in the cell structure as a part of the cell structure, (ii) a case where a pancreatic islet exists separately from a cell structure, and (iii) a case where some pancreatic islets form a cell structure by being included in the cell structure as a part of the cell structure, but remaining pancreatic islets exist separately from the cell structure. Alternately, all of the above-described (i) to (iii) may be within a range of the present invention. In addition, the pancreatic islet transplantation kit called in the present invention means a kit containing a cell structure and a pancreatic islet in a separate form, but in a state of being combined with each other.

The composition, the cell structure, and the pancreatic islet transplantation kit of the present invention include a "cell structure which contains a biocompatible macromolecular block and at least one kind of cell and in which a plurality of the above-described macromolecular blocks are arranged in gaps between a plurality of the above-described cells". Furthermore, the composition, the cell structure, and the pancreatic islet transplantation kit of the present invention further includes a pancreatic islet cell or a pancreatic islet in the cell structure or includes a pancreatic islet by combining the pancreatic islet with the cell structure. The composition, the cell structure, and the pancreatic islet transplantation kit of the present invention can achieve high glucose sensitivity of the pancreatic islet after transplantation by having the above-described constitution.

A cell structure, which contains cells and macromolecular blocks having biocompatibility, and in which the plurality of the above-described macromolecular block are arranged in gaps between the plurality of the above-described cells is disclosed in WO2011/108517A and JP2014-12114A. However, there is no disclosure that a specific combination called a pancreatic islet cell and a stem cell is used in a cell structure. Regarding the "cell structure having the biocompatible macromolecular block; and at least two kinds of cells, in which a plurality of the above-described macromolecular blocks are arranged in gaps between a plurality of the above-described cells, and the cell structure contains at least pancreatic islet cells and stem cells as the above-described cells" in the cell structure of the present invention, it is possible to achieve high glucose sensitivity by including both of the pancreatic islet cells and the stem cells in the macromolecular block. As can be seen from a contrast between Comparative Example A1 (only a pancreatic islet) and Comparative Example A3 (a cell structure formed of a pancreatic islet and a biocompatible macromolecular block) and a contrast between Comparative Example A4 (only a pancreatic islet cell) and Comparative Example A6 (a cell structure formed of a pancreatic islet cell and a biocompatible macromolecular block) in Examples to be described below in the present specification, it is shown that glucose sensitivity is decreased in a case of using a biocompatible macromolecular block, compared to a case of singly using a pancreatic islet or a pancreatic islet cell. Accordingly, the fact that the cell structure obtained by combining a pancreatic islet cell, a stem cell, and a biocompatible macromolecular block exhibits high glucose sensitivity is opposite to the finding that the glucose sensitivity is decreased in a case where a biocompatible macromolecular block is used, and is a totally unexpected and significant effect.

(1) Biocompatible Macromolecular Block

The composition, the cell structure, and the pancreatic islet transplantation kit of the present invention contain a biocompatible macromolecular block. The biocompatible macromolecular block will be described below.

(1-1) Biocompatible Macromolecules

Biocompatibility means a property which does not cause a significantly harmful reaction such as a long-term and chronic inflammatory reaction, during contact with a living body. Whether or not the biocompatible macromolecules used in the present invention are decomposed within a living body is not particularly limited as long as the biocompatible macromolecules have affinity to the living body. However, biodegradable macromolecules are preferable. Specific examples of non-biodegradable materials include polytetrafluoroethylene (PTFE), polyurethane, polypropylene, polyester, vinyl chloride, polycarbonate, acryl, stainless steel, titanium, silicone, and 2-methacryloyloxyethyl phosphorylcholine (MPC). Specific examples of the biodegradable materials include polypeptide (for example, gelatin or the like to be described below) such as recombinant peptide, polylactic acid, polyglycolic acid, lactic acid-glycolic acid copolymers (PLGA), hyaluronic acid, glycosaminoglycan, proteoglycan, chondroitin, cellulose, agarose, carboxymethyl cellulose, chitin, and chitosan. Among these, recombinant peptide is particularly preferable. Devising of an improvement of cell adhesion properties in these biocompatible macromolecules may be performed. Specifically, methods such as "coating of the surface of a base material with a cell adhesion substrate (fibronectin, vitronectin, or laminin) or peptides of a cell adhesion sequence (an RGD sequence, an LDV sequence, an REDV (SEQ ID NO: 2) sequence, a YIGSR (SEQ ID NO: 3) sequence, a PDSGR (SEQ ID NO: 4) sequence, an RYVVLPR (SEQ ID NO: 5) sequence, an LGTIPG (SEQ ID NO: 6) sequence, an RNIAEIIKDI (SEQ ID NO: 7) sequence, an IKVAV (SEQ ID NO: 8) sequence, an LRE sequence, a DGEA (SEQ ID NO: 9) sequence, and a HAV sequence, which are represented by one-letter notation of amino acids)", "aminization or cationization of the surface of a base material", or "plasma treatment performed on the surface of a base material or hydrophilic treatment due to corona discharge" can be used.

The kinds of polypeptides containing recombinant peptides are not particularly limited as long as polypeptides have biocompatibility. For example, gelatin, collagen, elastin, fibronectin, ProNectin, laminin, tenascin, fibrin, fibroin, entactin, thrombospondin, and RetroNectin are preferable and gelatin, collagen, and atelocollagen are most preferable. As the gelatin to be used in the present invention, natural gelatin or recombinant gelatin is preferable and recombinant gelatin is more preferable. The natural gelatin referred to herein means gelatin produced using naturally derived collagen. The recombinant gelatin will be described below in the present specification.

A "1/IOB" value which is a hydrophilic value of biocompatible macromolecules used in the present invention is preferably within a range of 0 to 1.0, more preferably within a range of 0 to 0.6, and still more preferably within a range of 0 to 0.4. IOB is an index of hydrophilic and hydrophobic properties based on an organic conceptual diagram representing polarity and non-polarity of an organic compound proposed by Atsushi HUJITA, and the details thereof are described in, for example, "Pharmaceutical Bulletin", vol. 2, 2, pp. 163-173 (1954), "Area of Chemistry" vol. 11, 10, pp. 719-725 (1957), and "Fragrance Journal, vol. 50, pp. 79-82 (1981). Briefly, the root of every organic compound is set to methane ($CH_4$), and all of other compounds are regarded as derivatives of methane. Certain numerical values for the number of carbons thereof, a substituent group, a transformation portion, a ring, and the like are set, and an organic value (OV) and an inorganic value (IV) are obtained by adding the score thereof. These values are plotted on a diagram in which the organic value is shown on the X-axis and the inorganic value is shown on the Y-axis. IOB in the organic conceptual diagram refers to a ratio of the inorganic value (IV) to the organic value (OV) in the organic conceptual diagram, that is, "inorganic value (IV)/organic value (OV)". The details of the organic conceptual diagram can be referred to "New Edition Organic Conceptual Diagram-Foundation and Application-" (written by Yoshio KOUDA, Sankyo Shuppan Co., Ltd., 2008). In the present specification, the hydrophilic and hydrophobic properties are represented by a "1/IOB" value which was obtained by taking a reciprocal number of JOB. This is a notation of representing more hydrophilic properties as the "1/IOB" value becomes small (close to 0).

The hydrophilic properties and water absorbency become high by making the "1/IOB" value of the macromolecules used in the present invention be within the above-described range, which effectively acts to hold nutrient components. As a result, it is estimated that this point contributes to stability of cells and easy survival of cells in a cell structure (mosaic cell aggregation) of the present invention.

In a case where the biocompatible macromolecules used in the present invention are polypeptides, the hydrophilic and hydrophobic indexes represented by a grand average of hydropathicity (GRAVY) value is preferably −9.0 to 0.3, and more preferably −7.0 to 0.0. The grand average of hydropathicity (GRAVY) value can be obtained through "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31:3784-3788 (2003)".

The hydrophilic properties and water absorbency become high by making the GRAVY value of the macromolecules used in the present invention be within the above-described range, which effectively acts to hold nutrient components. As a result, it is estimated that this point contributes to stability of cells and easy survival of cells in a cell structure (mosaic cell aggregation) of the present invention.

(1-2) Cross-Linking

The biocompatible macromolecules used in the present invention may be or may not be cross-linked, but are preferably cross-linked. By using the cross-linked biocompatible macromolecules, it is possible to obtain an effect of preventing instant decomposition during culturing in a medium and during transplantation into a living body. As a general cross-linking method, thermal cross-linking, cross-linking using aldehydes (for example, formaldehyde or glutaraldehyde), cross-linking using a condensation agent (carbodiimide, cyanamide, or the like), enzymatic cross-linking, photocrosslinking, ultraviolet cross-linking, a hydrophobic interaction, hydrogen bonding, an ionic interaction, and the like are known. In the present invention, it is preferable to use a cross-linking method in which glutaraldehyde is not used. In the present invention, it is more preferable to use a cross-linking method in which aldehydes or condensation agents are not used. That is, the biocompatible macromolecular blocks in the present invention are preferably biocompatible macromolecular blocks which do not contain glutaraldehyde, and are more preferably biocompatible macromolecular blocks which do not contain aldehydes or condensation agents. As the cross-linking method used in the present invention, thermal cross-linking, ultraviolet cross-linking, or enzymatic cross-linking is more preferable, and thermal cross-link is particularly preferable.

In a case of performing cross-linking using an enzyme, there is no particular limitation as long as the enzyme has a cross-linking action between macromolecular materials. However, it is possible to perform cross-linking preferably using transglutaminase and laccase and most preferably using transglutaminase. Specific examples of protein to be subjected to enzymatic cross-linking using transglutaminase are not particularly limited as long as the protein has a lysine residue and a glutamine residue. Transglutaminase may be derived from a mammal or may be derived from a microorganism. Specific examples thereof include mammal-derived transglutaminase which has been sold as Activa series manufactured by Ajinomoto Co., Inc., and a reagent; guinea pig liver-derived transglutaminase manufactured by, for example, Oriental Yeast Co., Ltd., Upstate USA Inc., or Biodesign International, Inc.; goat-derived transglutaminase; rabbit-derived transglutaminase; and human-derived blood coagulation factors (Factor XIIIa: Haematologic Technologies, Inc).

The reaction temperature when performing cross-linking (for example, thermal cross-linking) is not particularly limited as long as cross-linking can be performed, but is preferably −100° C. to 500° C., more preferably 0° C. to 300° C., still more preferably 50° C. to 300° C., still more preferably 100° C. to 250° C., and still more preferably 120° C. to 200° C.

(1-3) Recombinant Gelatin

The recombinant gelatin referred in the present invention means polypeptides or protein-like substances which have an amino acid sequence similar to that of gelatin produced through gene recombination technology. The recombinant gelatin which can be used in the present invention preferably has a repetition of a sequence (X and Y each independently show any amino acids) represented by Gly-X-Y which is characteristic to collagen. Here, a plurality of pieces of Gly-X-Y may be the same as or different from each other. Preferably, two or more sequences of cell adhesion signals are included in one molecule. As the recombinant gelatin used in the present invention, it is possible to use recombinant gelatin having an amino acid sequence derived from a partial amino acid sequence of collagen, and to use recombinant gelatin disclosed in, for example, EP1014176A2, U.S. Pat. No. 6,992,172B, WO2004/85473A, and WO2008/103041A. However, the recombinant gelatin is not limited thereto. Preferred recombinant gelatin used in the present invention is recombinant gelatin of the following aspect.

The recombinant gelatin is excellent in biocompatibility with original performance of natural gelatin, and is excellent in non-infection properties since there is no concern of bovine spongiform encephalopathy (BSE) and the recombinant gelatin with not being naturally derived. In addition, the recombinant gelatin is even compared to natural gelatin, and a sequence is determined. Therefore, it is possible to accurately design the strength and degradability so as to reduce deviation through cross-linking or the like.

The molecular weight of recombinant gelatin is not particularly limited, but is preferably 2 kDa to 100 kDa, more preferably 2.5 kDa to 95 kDa, still more preferably 5 kDa to 90 kDa, and most preferably 10 kDa to 90 kDa.

The recombinant gelatin preferably has a repetition of a sequence represented by Gly-X-Y which is characteristic to collagen. Here, a plurality of pieces of Gly-X-Y may be the same as or different from each other. In Gly-X-Y, Gly represents glycine and X and Y represent an arbitrary amino acid (preferably represents an arbitrary amino acid other than glycine). The sequence represented by Gly-X-Y characteristic to collagen is a partial structure which is extremely specific compared to other protein in a composition or a sequence of an amino acid of gelatin/collagen. In this section, glycine occupies about one third of the entirety of the amino acid sequence, one sequence is repeated every three sequences. Glycine is the simplest amino acid. Therefore, there is a little restraint in arrangement of molecular chains and glycine significantly contributes to regeneration of a helix structure during gelation. It is preferable that amino acids represented by X and Y contain many imino acids (proline and oxyproline) and occupy 10% to 45% of the entirety of the sequence. Preferably 80% or more of the sequence of the amino acids, more preferably 95% or more of the sequence of the amino acids, and most preferably 99% or more of the sequence of the amino acids in the recombinant gelatin has a repeating structure of Gly-X-Y.

In general gelatin, a polar amino acid with an electrical charge and a polar non-charged amino acid exist by 1:1 in polar amino acids. Here, the polar amino acid specifically indicates cysteine, aspartic acid, glutamic acid, histidine, lysine, asparagine, glutamine, serine, threonine, tyrosine, or arginine. Among these, the polar non-charged amino acid indicates cysteine, asparagine, glutamine, serine, threonine, or tyrosine. In recombinant gelatin used in the present invention, the proportion of the polar amino acid in the whole constituent amino acid is 10% to 40% and preferably 20% to 30%. It is preferable that the proportion of a non-charged amino acid in the polar amino acid is greater than or equal to 5% and less than 20% and preferably less than 10%. Furthermore, it is preferable that any one amino acid or preferably two or more amino acids among serine, threonine, asparagine, tyrosine, and cysteine are not contained on a sequence.

In general, in polypeptides, minimum amino acid sequences which work as cell adhesion signals are known (for example, Nagai Shoten Co., Ltd., "Pathophysiology", Vol. 9, No. 7 (1990) p. 527). The recombinant gelatin used in the present invention preferably has two or more these cell adhesion signals in one molecule. As the specific sequences, sequences such as an RGD sequence, an LDV sequence, an REDV (SEQ ID NO: 2) sequence, a YIGSR (SEQ ID NO: 3) sequence, a PDSGR (SEQ ID NO: 4) sequence, an RYVVLPR (SEQ ID NO: 5) sequence, an LGTIPG (SEQ ID NO: 6) sequence, an RNIAEIIKDI (SEQ ID NO: 7) sequence, an IKVAV (SEQ ID NO: 8) sequence, an LRE sequence, a DGEA (SEQ ID NO: 9) sequence, and a HAV sequence, which are represented by one-letter notation of amino acids are preferable in that there are many kinds of cells adhered. An RGD sequence, a YIGSR (SEQ ID NO: 3) sequence, a PDSGR (SEQ ID NO: 4) sequence, an LGTIPG (SEQ ID NO: 6) sequence, an IKVAV (SEQ ID NO: 8) sequence, and a HAV sequence are more preferable and an RGD sequence is particularly preferable. In the RGD sequence, an ERGD (SEQ ID NO: 10) sequence is preferable. It is possible to improve the production amount of substrate of a cell using recombinant gelatin having cell adhesion signals. For example, it is possible to improve the production of glycosaminoglycan (GAG) in a case of cartilage differentiation using mesenchymal stem cells as cells.

As arrangement of RGD sequences in recombinant gelatin used in the present invention, it is preferable that the number of amino acids between RGDs is between 0 to 100 and preferably between 25 to 60 without being even.

The content of this minimum amino acid sequence is preferably 3 to 50, more preferably 4 to 30, and particularly preferably 5 to 20 in one molecule of protein in view of cell adhesion properties and proliferation properties. The most preferable content thereof is 12.

In recombinant gelatin used in the present invention, the proportion of RGD motifs with respect to the total number of amino acids is preferably at least 0.4%. In a case where recombinant gelatin contains 350 or more amino acids, each stretch of the 350 amino acids preferably contains at least one RGD motif. The proportion of RGD motifs with respect to the total number of amino acids is still more preferably at least 0.6%, still more preferably at least 0.8%, still more preferably at least 1.0%, still more preferably at least 1.2%, and most preferably at least 1.5%. The number of RGD motifs within a recombinant peptides is, per 250 amino acids, preferably at least 4, still more preferably 6, still more preferably 8, and still more preferably 12 to 16. The proportion of RGD motifs being 0.4% corresponds to at least one RGD sequence per 250 amino acids. The number of RGD motifs is an integer, and therefore, gelatin formed of 251 amino acids needs to contain at least two RGD sequences in order to satisfy the characteristics of 0.4%. It is preferable that the recombinant gelatin of the present invention contains at least two RGD sequences per 250 amino acids, more preferably contains at least three RGD sequences per 250 amino acids, and still more preferably contains at least four RGD sequences per 250 amino acids. As a further mode of the recombinant gelatin of the present invention, the recombinant gelatin contains at least four RGD motifs, preferably 6 RGD motifs, more preferably 8 RGD motifs, and still more preferably 12 to 16 RGD motifs.

In addition, the recombinant gelatin may be partially hydrolyzed.

The recombinant gelatin used in the present invention is preferably represented by Formula: A-[(Gly-X-Y)$_n$]$_m$—B. n pieces of X each independently represent any amino acid and n pieces of Y each independently represent any amino acid. m is preferably 2 to 10 and more preferably 3 to 5. n is preferably 3 to 100, more preferably 15 to 70, and most preferably 50 to 65. A represents an arbitrary amino acid or an amino acid sequence, B represents an arbitrary amino acid or an amino acid sequence, n pieces of X each independently represent any amino acid, and n pieces of Y each independently represent any amino acid.

More preferably, the recombinant gelatin used in the present invention is represented by Formula: Gly-Ala-Pro-[(Gly-X-Y)$_{63}$]$_3$-Gly (SEQ ID NO: 11) (where 63 pieces of X each independently represent any amino acid and 63 pieces of Y each independently represent any amino acid. 63 pieces of Gly-X-Y may be the same as or different from each other).

It is preferable that a plurality of sequence units of collagen which naturally exists are bonded to a repeating unit. Any naturally existing collagen referred to herein may be used as long as the collagen naturally exists, but is preferably I type collagen, II type collagen, III type collagen, IV type collagen, or V type collagen, and more preferably I type collagen, II type collagen, or III type collagen. According to another form, the above-described collagen is preferably derived from a human, cattle, a pig, a mouse, or a rat, and is more preferably derived from a human.

An isoelectric point of the recombinant gelatin used in the present invention is preferably 5 to 10, more preferably 6 to 10, and still more preferably 7 to 9.5.

It is preferable that the recombinant gelatin is not deaminated.

It is preferable that the recombinant gelatin does not have a telopeptide.

It is preferable that the recombinant gelatin is a substantially pure polypeptide which is prepared using a nucleic acid encoding an amino acid sequence.

It is particularly preferable that the recombinant gelatin used in the present invention is any of
(1) a peptide formed of an amino acid sequence described in SEQ ID No: 1;
(2) a peptide which is formed of an amino acid sequence in which one or a plurality of amino acids are deleted, substituted, or added in the amino acid sequence described in SEQ ID No: 1, and has biocompatibility; or
(3) a peptide which is formed of an amino acid sequence having 80% or more (more preferably 90% or more, particularly preferably 95% or more, and most preferably 98% or more) sequence identity to the amino acid sequence described in SEQ ID No: 1, and has biocompatibility.

"One or a plurality of" in the "amino acid sequence in which one or a plurality of amino acids are deleted, substituted, or added" preferably means 1 to 20 amino acids, more preferably means 1 to 10 amino acids, still more preferably means 1 to 5 amino acids, and particularly preferably means 1 to 3 amino acids.

The recombinant gelatin used in the present invention can be produced through gene recombination technology which is known to those skilled in the art, and can be produced in accordance with, for example, methods disclosed in EP1014176A2, U.S. Pat. No. 6,992,172B, WO2004/85473A, and WO2008/103041A. Specifically, a gene encoding an amino acid sequence of predetermined recombinant gelatin is acquired, the acquired gene is incorporated into an expression vector to produce a recombinant expression vector, and a transformant is produced by introducing the recombinant expression vector into an appropriate host. The recombinant gelatin is produced by culturing the obtained transformant in an appropriate medium. Therefore, it is possible to prepare the recombinant gelatin used in the present invention by collecting the recombinant gelatin produced from a culture product.

(1-4) Biocompatible Macromolecular Block

In the present invention, a block (aggregation) formed of the above-described biocompatible macromolecules is used.

The shape of the biocompatible macromolecular block in the present invention is not particularly limited. Examples thereof include an amorphous shape, a spherical shape, a particulate shape (granule), a powdery shape, a porous shape, a fibrous shape, a spindle shape, a flat shape, and a sheet shape. An amorphous shape, a spherical shape, a particulate shape (granule), a powdery shape, and a porous shape are preferable. The amorphous shape indicates that the shape of a surface is uneven, and indicates, for example, an object, such as rock, which has roughness.

The size of one biocompatible macromolecular block in the present invention is not particularly limited, but is preferably 1 μm to 1000 μm, more preferably 10 μm to 1000 μm, still more preferably 10 μm to 700 μm, still more preferably 10 μm to 300 μm, still more preferably 10 μm to 200 μm, still more preferably 20 μm to 200 μm, still more preferably 20 μm to 150 μm, and still more preferably 50 μm to 110 μm. It is possible to achieve more excellent glucose sensitivity by setting the size of one biocompatible macromolecular block to be within the above-described range. The size of one biocompatible macromolecular block does not mean that an average value of the sizes of a plurality of biocompatible macromolecular blocks is within the above-described range, but means the size of each biocompatible macromolecular block which is obtained by sieving a plurality of biocompatible macromolecular blocks.

The size of one block can be defined by the size of a sieve used when dividing the block. For example, blocks remaining on a sieve with 106 μm when blocks which have been passed through a sieve with 180 μm for sifting are sifted using the sieve with 106 μm can be regarded as blocks having a size of 106 to 180 μm. Next, blocks remaining on a sieve with 53 μm when blocks which have been passed through the sieve with 106 μm for sifting are sifted using the sieve with 53 μm can be regarded as blocks having a size of 53 to 106 μm. Next, blocks remaining on a sieve with 25 μm when blocks which have been passed through the sieve with 53 μm for sifting are sifted using the sieve with 25 μm can be regarded as blocks having a size of 25 to 53 μm.

(1-5) Method for Producing Biocompatible Macromolecular Block

The method for producing a biocompatible macromolecular block is not particularly limited. For example, it is possible to obtain a biocompatible macromolecular block by pulverizing a porous body of biocompatible macromolecules in a granular form using a pulverizer (such as NEW POWERMILL).

When producing a porous body of biocompatible macromolecules, shape of ice to be formed becomes a spherical shape due to inclusion of a freezing step in which the liquid temperature (highest internal liquid temperature) in a portion having the highest liquid temperature within a solution becomes lower than or equal to a "melting point of a solvent −3° C." in an unfrozen state. A porous body having spherical isotropic hollow holes (spherical holes) is obtained when the ice is dried through this step. The shape of the ice to be formed becomes a columnar or tabular shape when the ice is frozen without including a freezing step in which the liquid temperature (highest internal liquid temperature) in a portion having the highest liquid temperature within a solution becomes higher than or equal to a "melting point of a solvent −3° C." in an unfrozen state. A porous body having columnar or tabular hollow holes (columnar or tabular holes) which are uniaxially or biaxially long is obtained when the ice is dried through this step.

In the present invention, it is preferable that it is possible to produce biocompatible macromolecular blocks through a method including a step (a) of freezing a solution of biocompatible macromolecules through freezing treatment in which the highest internal liquid temperature, which is a liquid temperature in a portion having the highest liquid temperature within the solution, becomes lower than or equal to a temperature (a "melting point of a solvent −3° C.") which is 3° C. lower than a melting point of a solvent in an unfrozen state; and a step (b) of freeze-drying the frozen biocompatible macromolecules which have been obtained in the above-described step (a).

In the present invention, it is more preferable that it is possible to produce biocompatible macromolecular blocks in a granular form by pulverizing the porous body obtained in the above-described step (b).

It is more preferable that it is possible to freeze the solution of the biocompatible macromolecules through freezing treatment in which the highest internal liquid temperature, which is a liquid temperature in a portion having the highest liquid temperature within the solution, becomes lower than or equal to a temperature ("melting point of a solvent −7° C.") which is 7° C. lower than a melting point of a solvent in an unfrozen state, in the above-described step (a).

(2) Pancreatic Islet and Pancreatic Islet Cell

The composition, the cell structure, and the pancreatic islet transplantation kit of the present invention contain a pancreatic islet or a pancreatic islet cell.

The pancreatic islet is a cell aggregation constituted of about 2000 pancreatic islet cells in average which is also called a Langerhans' islet as another name. The pancreatic islet is constituted of five types of cells of an α cell which secretes glucagon, a β cell which secretes insulin, a δ cell which secretes somatostatin, an ε cell which secretes ghrelin, and a pancreatic polypeptide (PP) cell which secretes pancreatic polypeptide.

The pancreatic islet cell referred to in the present invention may contain at least one of the above-described five types of cells, and preferably contains at least a β cell. A mixture containing all of an α cell, a β cell, a δ cell, an ε cell, and a PP cell may be used as the pancreatic islet cell.

In addition, the pancreatic islet cell of the present invention may be a pancreatic islet cell obtained through differentiation. For example, the pancreatic islet cell is set to include a pancreatic islet cell obtained by differentiating an iPS cell, an ES cell, or a somatic stem cell such as a mesenchymal stem cell.

The pancreatic islet or the pancreatic islet cell used in the present invention preferably has viability and a function to a degree that a pathological condition of a patient can be recovered in a case of being transplanted into the patient. Preferred functions of the pancreatic islet or the pancreatic islet cell include secreting insulin and maintaining glucose sensitivity even after transplantation. The glucose sensitivity will be described below in the present specification.

(3) Cell Other Than Pancreatic Islet Cell

In the present invention, in some cases, cells other than pancreatic islet cells are used.

In the composition and the pancreatic islet transplantation kit of the present invention including: A: a cell structure which contains a biocompatible macromolecular block and at least one kind of cell and in which a plurality of the above-described macromolecular blocks are arranged in gaps between a plurality of the above-described cells; and B: a pancreatic islet, a pancreatic islet cell and/or a cell other than the pancreatic islet cell can be used as the above-described "at least one kind of cell", but a cell other than a pancreatic islet cell can be preferably used as the above-described "at least one kind of cell".

In addition, in the cell structure of the present invention including: a biocompatible macromolecular block; at least one kind of cell; and a pancreatic islet, in which a plurality of the above-described macromolecular blocks are arranged in gaps between a plurality of the above-described cells, a pancreatic islet cell and/or a cell other than the pancreatic islet cell can be used as the above-described "at least one kind of cell", but a cell other than a pancreatic islet cell can be preferably used as the above-described "at least one kind of cell".

Furthermore, in the cell structure including: a biocompatible macromolecular block; and at least two kinds of cells, in which a plurality of the above-described macromolecular blocks are arranged in gaps between a plurality of the above-described cells, and the cell structure contains at least pancreatic islet cells and stem cells as the above-described cells, a stem cell is used as the cell other than the pancreatic islet cell.

As a cell other than a pancreatic islet cell, it is possible to use arbitrary cells as long as cell transplantation can be performed, and the kinds thereof are not particularly limited. In addition, one kind of cell may be used or a plurality of kinds of cells may be used in combination. In addition, cells to be used are preferably animal cells, more preferably vertebrate animal-derived cells, and particularly preferably human-derived cells. The kinds of vertebrate animal-derived cells (particularly human-derived cells) may be either of stem cells (for example, pluripotent cells or somatic stem cells), precursor cells, and mature cells. As the pluripotent cells, it is possible to use, for example, embryonic stem (ES) cells, germline stem (GS) cells, or induced pluripotent stem (iPS) cells. As the somatic stem cells, it is possible to use, for example, mesenchymal stem cells (MSC), hematopoietic stem cells, amniotic cells, cord blood cells, bone marrow-derived cells, cardiac muscle stem cells, adipose-derived stem cells, or neural stem cells.

As the precursor cells and mature cells, it is possible to use, for example, cells derived from the skin, the dermis, the epidermis, muscles, cardiac muscles, nerves, bones, cartilage, the endothelium, the brain, epithelium, the heart, the kidney, the liver, the spleen, the inside of the oral cavity, the cornea, bone marrow, cord blood, amnion, or hair. As the human-derived cells, it is possible to use, for example, ES cells, iPS cells, MSC, chondrocytes, osteoblasts, osteoprogenitor cells, mesenchyme cells, myoblasts, cardiac muscle cells, cardiac myoblasts, nerve cells, liver cells, fibroblasts, corneal endothelial cells, vascular endothelial cells, corneal epithelial cells, amniotic cells, cord blood cells, bone marrow-derived cells, or hematopoietic stem cells. In addition, the cells may be derived from any of autologous cells or heterologous cells. Among these, it is possible to use, for example, ES cells, iPS cells, and mesenchymal stem cells (MSC), and it is preferable to use MSC.

(4) Cell Structure

In the present invention, the cell structure can have a thickness suitable for cell transplantation by three-dimensionally arranging a plurality of biocompatible macromolecular blocks in gaps between a plurality of cells in a mosaic shape using the biocompatible macromolecular blocks and the cells. Furthermore, a cell structure in which cells evenly exist in the structure is formed by three-dimensionally arranging the biocompatible macromolecular blocks and the cells in a mosaic shape, and it is possible to deliver nutrients to the inside of the cell structure from the outside.

In the cell structure of the present invention, the plurality of biocompatible macromolecular blocks are arranged in gaps between the plurality of cells. Here, the "gaps between cells" is not necessarily a space closed by the constituent cells, and may be interposed by the cells. Gaps are not necessarily present between all of the cells, and there may be a place where cells are brought into contact with each other. The distance of gaps between cells through biocompatible macromolecular blocks, that is, the gap distance when selecting a certain cell, and a cell existing in a shortest distance from the certain cell is not particularly limited. However, the distance is preferably the size of a biocompatible macromolecular block, and a favorable distance is also within the range of the favorable size of a biocompatible macromolecular block.

In addition, the biocompatible macromolecular blocks have a configuration of being interposed by the cells. However, there are not necessarily cells between all of the biocompatible macromolecular blocks, and there may be a place where biocompatible macromolecular blocks are brought into contact with each other. The distance between biocompatible macromolecular blocks through cells, that is, the distance when selecting a biocompatible macromolecular block, and a biocompatible macromolecular block existing in a shortest distance from the biocompatible macromolecular block is not particularly limited. However, the distance is preferably the size of an aggregation of cells when one or several cells to be used are gathered. For example, the size thereof is preferably 10 μm to 1000 μm, more preferably 10 μm to 200 μm, and still more preferably 50 μm to 110 μm.

The expressions such as "evenly exist", for example, the "cell structure in which cells evenly exist in the structure" is used in the present specification. However, the expression does not mean complete evenness, but means that it is possible to deliver nutrients to the inside of the cell structure from the outside.

The thickness or the diameter of the cell structure in the present invention can be set to a desired thickness. As the lower limit, being greater than or equal to 100 μm is preferable, being greater than or equal to 200 μm is more preferable, being greater than or equal to 215 μm is still more preferable, being greater than or equal to 400 μm is still more preferable, and being greater than or equal to 730 μm is most preferable. The upper limit of the thickness or the diameter is not particularly limited, but a general range in use is preferably less than or equal to 3 cm, more preferably less than or equal to 2 cm, and still more preferably less than or equal to 1 cm. In addition, the range of the thickness or the diameter of the cell structure is preferably 100 μm to 3 cm and more preferably 200 μm to 2 cm. By setting the thickness or the diameter of the cell structure to be within the above-described range, it is possible to achieve more excellent glucose sensitivity.

However, in the (ii) case where a pancreatic islet exists separately from a cell structure, the thickness or the diameter of the cell structure is preferably set to be the same as the size of the pancreatic islet. Specifically, 100 μm to 400 μm is preferable, 150 μm to 300 μm is more preferable, and 150 μm to 250 μm is still more preferable.

In the cell structure of the present invention, a region formed of biocompatible macromolecular blocks and a region formed of cells are preferably arranged in a mosaic shape. The "thickness or the diameter of cell structure" in the present specification indicates the following. When selecting a certain point A in the cell structure, the length of a line segment which divides the cell structure is set as a line segment A such that the distance from the external boundary of the cell structure becomes shortest within a straight line passing through the point A. A point A at which the line segment A thereof in the cell structure becomes longest is selected, and the length of the line segment A during the selection thereof is set as the "thickness or the diameter of the cell structure".

In the cell structure in the present invention, the ratio of a biocompatible macromolecular block to a cell is not particularly limited. However, the ratio of a biocompatible macromolecular block per cell is preferably 0.0000001 μg to 1 μg, more preferably 0.000001 μg to 0.1 μg, still more preferably 0.00001 μg to 0.01 μg, and most preferably 0.00002 μg to 0.006 μg. In a case where the cell structure of the present invention includes two or more types of cells, the above-described "per cell" means "per cell with respect to all cells". For example, in the case of the cell structure including: a biocompatible macromolecular block; and at least two kinds of cells, in which a plurality of the above-described macromolecular blocks are arranged in gaps between a plurality of the above-described cells, and the cell structure contains at least pancreatic islet cells and stem cells as the above-described cells, the cell structure preferably contains 0.0000001 μg to 1 μg of a biocompatible macromolecular block per cell with respect to all cells including pancreatic islet cells and stem cells. In the case of the "cell structure including: a biocompatible macromolecular block; at least one kind of cell; and a pancreatic islet, in which a plurality of the above-described macromolecular blocks are arranged in gaps between a plurality of the above-described cells", a cell (pancreatic islet cell) included in the pancreatic islet is considered not to be included in the "cell" of the above-described "per cell".

By setting the ratio of the biocompatible macromolecular blocks to the cells to be within the above-described range, it is possible to make the cells more evenly exist, which is preferable. By setting the lower limit to be within the above-described range, it is possible to exhibit an effect of the cells when using the cells for the above-described purpose. Moreover, by setting the upper limit to be within the above-described range, it is possible to supply components in arbitrarily existing biocompatible macromolecular blocks to cells. Here, the components in biocompatible macromolecular blocks are not particularly limited, but examples thereof include components contained in a medium to be described below.

In the case of the cell structure including: a biocompatible macromolecular block; and at least two kinds of cells, in which a plurality of the above-described macromolecular blocks are arranged in gaps between a plurality of the above-described cells, and the cell structure contains at least pancreatic islet cells and stem cells as the above-described cells, the cell structure preferably contains 10% by number to 90% by number of pancreatic islet cells, more preferably contains 20% by number to 80% by number of pancreatic islet cells, still more preferably contains 30% by number to 70% by number of pancreatic islet cells, and particularly preferably contains 40% by number to 60% by number of pancreatic islet cells, with respect to all the cells containing the pancreatic islet cells and the stem cells. It is preferable that the ratio of the pancreatic islet cells is within the above-described range from the viewpoint of achieving high glucose sensitivity.

In the cell structure of the present invention, SI represented by the following equation is preferably greater than or equal to 3.0 and more preferably greater than or equal to 3.1. The upper limit value of SI is not particularly limited, but in general, is less than or equal to 50 and more preferably less than or equal to 20.

$$SI = \text{amount of insulin during culture in 20 mM glucose medium/amount of insulin during culture in 3 mM glucose medium}$$

The amount of insulin can be measured through the following method. The cell structure is cultured in a 3 mM glucose medium for a first one hour and the secretion amount of insulin is stabilized. The cell structure is cultured in a 3 mM glucose medium for a next one hour and the secretion amount of insulin is measured in glucose at a low concentration. The cell structure is cultured in a 20 mM glucose medium for the last one hour and the secretion amount of insulin is measured in glucose at a high concentration. It is possible to produce the 20 mM glucose medium as a medium using a 3 mM glucose-containing medium (manufactured by COSMO BIO co., ltd.: PNI14) after adding a glucose solution to this medium. During the measurement, 400 µL of a medium with each glucose concentration is added to each well of a cell container (such as 6.5 mm Transwell (registered trademark) with 5.0 µm Pore Polycarbonate Membrane Insert, Sterile (manufactured by Corning) in which a filter-attached insert becomes a set with a 24-well plate), 100 µL of a 3 mM glucose-containing medium (manufactured by COSMO BIO co., ltd.: PNI14) containing five cell structures is washed with 1 ml of the same medium, and 100 µL of the above-described medium containing five cell structures is placed on the insert. The insert is moved every hour, 400 µL of the medium in the well after moving the insert is collected, and insulin is quantitatively determined through enzyme-linked immunosorbent assay (ELISA). In ELISA, it is possible to use Rat Insulin ELISA (manufactured by ALPCO).

(5) Method for Producing Cell Structure

The cell structure of the present invention can be produced by mixing a biocompatible macromolecular block with at least one kind of cell and a pancreatic islet as desired. More specifically, the cell structure of the present invention can be produced by alternately arranging a biocompatible macromolecular block and the above-described cell. The production method is not particularly limited, but is preferably a method for forming a biocompatible macromolecular block, and then, mixing the biocompatible macromolecular block with a cell and a pancreatic islet as desired. Specifically, it is possible to produce the cell structure of the present invention by incubating a mixture of a biocompatible macromolecular block, a cell-containing culture solution, and a pancreatic islet as desired. For example, in the solution held by a container, in the container, a cell and the biocompatible macromolecular block are arranged in a mosaic shape. It is preferable to promote or control the formation of the sequence, which is formed of a cell and a biocompatible base material, in a mosaic shape, through natural aggregation, natural fall, centrifugation, or agitation as means for the arrangement.

As the container to be used, a container formed of a low-adhesive cell material or a non-adhesive cell material is preferable and a container formed of polystyrene, polypropylene, polyethylene, glass, polycarbonate, or polyethylene terephthalate is more preferable. The shape of the bottom surface of a container is preferably a flat bottom shape, a U-shape, and a V-shape.

In the cell structure (mosaic cell aggregation) obtained through the above-described method, it is possible to produce a cell structure having a desired size through a method, for example, (a) merging cell structures (mosaic cell aggregations), which have been separately prepared, with each other, or (b) increasing the volume of the structure under a differentiation medium or a proliferation medium.

The method for merging the cell structures with each other or the method for increasing the volume of the cell structure is not particularly limited.

For example, it is possible to increase the volume of the cell structure by exchanging a medium with a differentiation medium or a proliferation medium in a step of incubating a mixture of a biocompatible macromolecular block and a cell-containing culture solution. Preferably, it is possible to produce a cell structure in which cells evenly exist and which has a desired size, by further adding a biocompatible macromolecular block, in the step of incubating a mixture of a biocompatible macromolecular block and a cell-containing culture solution.

In a case where cell structures which have been separately prepared are merged with each other, it is possible to, for example, merge a plurality of cell structures which contains a plurality of biocompatible macromolecular blocks and a plurality of cells and in which one or a plurality of the above-described biocompatible macromolecular blocks are arranged in some or all of a plurality of gaps formed by the plurality of the above-described cells. A cell structure obtained by merging a plurality of cell structures of the present invention with each other as described in the above-described (a) is also within the scope of the present invention.

The thickness or the diameter of each cell structure before the above-described merging is preferably 10 µm to 1 cm, more preferably 10 µm to 2000 µm, still more preferably 15 µm to 1500 µm, and most preferably 20 µm to 1300 µm. The thickness or the diameter thereof after the merging is preferably 400 µm to 3 cm, more preferably 500 µm to 2 cm, and still more preferably 720 µm to 1 cm.

However, in the (ii) case of the embodiment where a pancreatic islet exists separately from a cell structure, the thickness or the diameter of the cell structure after the merging is preferably set to be the same as the size of the pancreatic islet as described above. Specifically, 100 µm to 400 µm is preferable, 150 µm to 300 µm is more preferable, and 150 µm to 250 µm is still more preferable. A preferred range of the thickness or the diameter of each cell structure before merging is within the above-described favorable range of the thickness or the diameter of the cell structure after the merging.

Examples of a method for producing the cell structure including: a biocompatible macromolecular block; at least one kind of cell; and a pancreatic islet, in which a plurality of the above-described macromolecular blocks are arranged in gaps between a plurality of the above-described cells include (i) a method for producing a cell structure by incubating a pancreatic islet and a cell structure which has been obtained after producing a cell structure containing no pancreatic islet using the biocompatible macromolecular block and at least one type of cell, through the above-described method and (ii) a method for producing a cell structure by incubating a biocompatible macromolecular block, at least one type of cell, and a pancreatic islet. In a case of using the cell structure of the present invention as a hypoglycemic agent, the cell structure including: a biocompatible macromolecular block; at least one kind of cell; and a pancreatic islet, in which a plurality of the above-described macromolecular blocks are arranged in gaps between a plurality of the above-described cells is particularly preferable. Among these, the cell structure produced through the above-described (i) method is more preferable.

[Pancreatic Islet Cell Transplantation Treatment Agent and Hypoglycemic Agent]

The composition, the cell structure, or the pancreatic islet transplantation kit of the present invention can be used as a pancreatic islet cell transplantation treatment agent or a hypoglycemic agent.

In a case where the composition, the cell structure, or the pancreatic islet transplantation kit of the present invention is used as a pancreatic islet cell transplantation treatment agent, it is possible to administer these to a diabetic patient, a patient whose pancreas is completely removed, or the like. In a case of using the composition, the cell structure, or the pancreatic islet transplantation kit of the present invention as a hypoglycemic agent, for example, it is possible to administer these to a patient, such as an insulin-dependent diabetic patient and a patient whose pancreas is completely removed, who requires reduction in blood sugar and whose blood sugar is higher than a normal value.

As the transplantation method, it is possible to use a method using incision, injection, or an endoscope. In the cell structure of the present invention, it is possible to reduce the size of the structure unlike a cell-transplanted substance such as a cell sheet, and therefore, it is possible to perform less invasive transplantation method such as transplantation performed through injection.

The transplantation site is not particularly limited and examples thereof include under the skin, within the liver, within the muscle, within the greater omentum, or under the renal capsule. However, in the case of using the present invention as a pancreatic islet cell transplantation treatment agent, it is preferable to transplant the present invention under the skin or into the muscle.

The number of pancreatic islet cells and the number of pancreatic islets in the pancreatic islet cell transplantation treatment agent and the hypoglycemic agent of the present invention can be set to the number of pancreatic islet cells and the number of pancreatic islets which have been calculated such that a desired treatment effect is produced. The number of pancreatic islet cells per administration of the pancreatic islet cell transplantation treatment agent and the hypoglycemic agent of the present invention is preferably about $5.0 \times 10^6$ to $1.2 \times 10^8$ pieces/kg body weight per 1 kg of the body weight of a patient, more preferably about $8.0 \times 10^6$ to $8.0 \times 10^7$ pieces/kg body weight per 1 kg of the body weight of a patient, still more preferably about $1.2 \times 10^7$ to $4.0 \times 10^7$ pieces/kg body weight per 1 kg of the body weight of a patient. In addition, the number of pancreatic islets per administration is preferably about 5000 to 60000 pieces/kg body weight per 1 kg of the body weight of a patient, more preferably about 8000 to 40000 pieces/kg body weight per 1 kg of the body weight of a patient, and still more preferably about 12000 to 20000 pieces/kg body weight per 1 kg of the body weight of a patient.

According to the present invention, there is provided a cell transplantation method including a step of transplanting the composition, the cell structure, or the pancreatic islet transplantation kit of the present invention into a patient who requires transplantation of a pancreatic islet or a pancreatic islet cell. According to the present invention, there is provided a cell transplantation method including a step of transplanting the composition, the cell structure, or the pancreatic islet transplantation kit of the present invention into a patient who requires reduction in blood sugar.

According to the present invention, use of the composition, the cell structure, or the pancreatic islet transplantation kit of the present invention for producing a cell transplantation treatment agent is further provided. According to the present invention, there is provided use of the composition, the cell structure, or the pancreatic islet transplantation kit of the present invention for producing a hypoglycemic agent.

A second aspect of the present invention is the aspect described in the above-described (51) to (80). Hereinafter, a second aspect of the present invention will be described.

[Composition and Kit]

The composition of the present invention is a composition containing a pancreatic islet; and a spheroid formed of at least one type of stem cell. The kit of the present invention is a kit containing a pancreatic islet; and a spheroid formed of at least one type of stem cell.

The composition referred to in the present invention means an arbitrary composition containing a pancreatic islet; and a spheroid formed of at least one type of stem cell, and the form of the composition is not particularly limited. For example, the composition may be a liquid composition containing a plurality of pancreatic islets and a plurality of spheroids in a liquid, or a composition formed of only a cell containing a plurality of pancreatic islets and a plurality of spheroids. The composition of the present invention is preferably the liquid composition containing a plurality of pancreatic islets and a plurality of spheroids in a liquid and is more preferably a composition containing a plurality of pancreatic islets and a plurality of spheroids in a liquid medium. In a case where the composition of the present invention is the composition containing a plurality of pancreatic islets and a plurality of spheroids in a liquid medium, the plurality of pancreatic islets and the plurality of spheroids may form a cell aggregation in the liquid medium or may float in the liquid medium. In addition, a state where a plurality of pancreatic islets and a plurality of spheroids form a cell aggregation in a liquid medium and a state where a plurality of pancreatic islets and a plurality of spheroids float in a liquid medium may coexist with each other.

The kit referred to in the present invention means a kit containing a pancreatic islet; and a spheroid formed of at least one type of stem cell in separate form, but in a state of being combined with each other.

A characteristic of the composition and the kit of the present invention is to use a spheroid formed of at least one type of stem cell. In the present invention, an effect of capable of improving glucose sensitivity using a stem cell in which a spheroid is formed without using stem cells in a dispersed state is exhibited. Exhibiting the above-described effect using a combination of a pancreatic islet and a spheroid formed of a stem cell is totally unexpected.

In general, there is a (1) purpose of inducing differentiation of a cell or a (2) purpose of imparting polarity to a cell as a purpose of a case of spheroidizing a cell. As (1), it is possible to, for example, differentiate mesenchymal stem cells into chondrocytes by culturing the mesenchymal stem cells in a spheroid state. As (2), it is possible to, for example, recover polarity which has been originally possessed by liver cells within a living body, by culturing the liver cells in a spheroid state. However, these two purposes are not required in stem cells used together with pancreatic islets in the present invention. It is unnecessary to be intended to differentiate mesenchymal stem cells and there is also no relation in polarity in a case of using one type of cell. Accordingly, in the present invention, there is no motivation to spheroidize stem cells to be used together with pancreatic islets.

(1) Pancreatic Islet

The composition and the kit of the present invention contain a pancreatic islet.

The pancreatic islet is a cell aggregation constituted of about 2000 pancreatic islet cells in average which is also called a Langerhans' islet as another name. The pancreatic islet is a cell aggregate constituted of five types of cells of an α cell which secretes glucagon, a β cell which secretes insulin, a δ cell which secretes somatostatin, an ε cell which secretes ghrelin, and a pancreatic polypeptide (PP) cell which secretes pancreatic polypeptide.

The pancreatic islet used in the present invention preferably has viability and a function to a degree that a pathological condition of a patient can be recovered in a case of being transplanted into the patient. Preferred functions of the pancreatic islet or include secreting insulin and maintaining glucose sensitivity even after transplantation. The glucose sensitivity will be described below in the present specification.

The number of pancreatic islets in the composition and the kit of the present invention is not particularly limited, can be set to the number of pancreatic islets which have been calculated such that a desired treatment effect is produced.

The composition and the kit of the present invention can be used for transplanting a pancreatic islet into a living body. It is possible to reduce a blood sugar level of a living body using the composition and the kit of the present invention for transplanting a pancreatic islet into the living body. Measurement of the blood sugar level of the living body can be performed through a usual method. For example, it is possible to measure the blood sugar level of an experimental animal such as a mouse using a commercially available glucose concentration measuring device such as GLUCOSE PILOT (manufactured by IWAI CHEMICALS COMPANY) and to measure the blood sugar level of a human using a commercially available glucose concentration measuring device such as ONE TOUCH ULTRAVIEW (Johnson & Hohnson K.K.) or ACCU-CHEK (Roche Diagnostics K.K.).

(2) Spheroid Formed of Stem Cell

The composition and the kit of the present invention contain a spheroid formed of at least one type of stem cell.

An arbitrary stem cell can be used as long as it is possible to perform cell transplantation, and the type of the stem cell is not particularly limited. In addition, one type of stem cell may be used or a combination of a plurality of types of stem cells may be used. However, it is preferable to use one type of stem cell. That is, in the present invention, it is preferable to use a spheroid formed of one type of stem cell.

The stem cell to be used is preferably an animal cell, more preferably a vertebrate-derived cell, and a particularly preferably a human-derived cell. As an example of the stem cell, any one of a pluripotent cell and a somatic stem cell may be used. As the pluripotent cell, it is possible to use, for example, an embryonic stem (ES) cell, a germline stem (GS) cell, or an induced pluripotent stem (iPS) cell. As the somatic stem cell, it is possible to use, for example, a mesenchymal stem cell (MSC), hematopoietic stem cell, an amniotic cell, a cord blood cell, a bone marrow-derived cell, a cardiac muscle stem cell, an adipose-derived stem cell, or a neural stem cell. In addition, the cells may be derived from any one of autologous cells and heterologous cells. Among the above-described cells, it is possible to use, for example, an ES cell, an iPS cell, or a mesenchymal stem cell (MSC), and MSC is preferable.

The spheroid means a cell aggregate in which cells are three-dimensionally aggregated. It is preferable that the spheroid according to the present invention is a cell aggregate which does not contain other components and in which cells are three-dimensionally aggregated using only the cells.

The size and the shape of a spheroid is not particularly limited, but is preferably the same as the size of a pancreatic islet. The shape and the size of spheroid are not particularly limited. However, the shape and the size of spheroid can be set to, for example, preferably a spherical shape having a diameter of 100 μm to 500 μm and more preferably to a spherical shape having a diameter of 100 μm to 300 μm. As the method for measuring the size of a spheroid, it is possible to measure the size of a spheroid through approximating the spherical spheroid to a sphere and measuring the diameter of the approximated sphere, in a case where the spheroid is spherical.

After adjusting the number of stem cells to a predetermined number (for example, $5\times10^1$ cells/mL to $1\times10^4$ cells/mL) using a medium, it is possible to produce a spheroid through culturing the stem cells in the medium in an adequate culture container. It is preferable to use a medium (proliferation medium), in which stem cells can be proliferated, as the medium. It is possible to use MSCGM BulletKit (registered trademark) manufactured by TAKARA BIO INC.), a StemPro MSC SFM XenoFree medium (life technologies, A10675-01), or the like as the proliferation medium of stem cells, but there is no particular restriction. The culture container is not particularly limited as long as it is possible to culture stem cells. However, a container formed of a low-adhesive cell material or a non-adhesive cell material is preferable and a container formed of polystyrene, polypropylene, polyethylene, glass, polycarbonate, or polyethylene terephthalate is more preferable. The shape of the bottom surface of a container is preferably a flat bottom shape, a U-shape, and a V-shape. It is possible to produce a spherical spheroid using a U-shaped plate (for example, Sumilon Celltight X96U plate (of which the bottom is in a U-shape and which is manufactured by Sumitomo Bakelite Co., Ltd.)).

The number of cells per spheroid in the composition and the kit of the present invention is preferably $5 \times 10^1$ cells to $1 \times 10^4$ cells, more preferably $1 \times 10^2$ cells to $5 \times 10^3$ cells, and still more preferably $2 \times 10^2$ cells to $2 \times 10^3$ cells.

The number of spheroids in the composition and the kit of the present invention with respect to the number of pancreatic islets is preferably 0.1:1 to 20:1, more preferably 0.5:1 to 10:1, and still more preferably 1:1 to 5:1 ("0.5:1" means that the number of spheroids is 0.5 in a case where the number of pancreatic islets is set to 1).

(3) Composition

In the composition of the present invention, SI represented by the following equation is preferably greater than or equal to 1.7 and more preferably greater than or equal to 2.0. The upper limit value of SI is not particularly limited, but is, in general, less than or equal to 50 and more preferably less than or equal to 20.

SI=amount of insulin during culture in 20 mmol/L glucose medium/amount of insulin during culture in 3 mmol/L glucose medium The amount of insulin can be measured through the following method. A cell aggregation formed using the composition of the present invention is cultured in a 3 mmol/L glucose medium for a first one hour and the secretion amount of insulin is stabilized. The cell aggregation is cultured in a 3 mmol/L glucose medium for a next one hour and the secretion amount of insulin is measured in glucose at a low concentration. The cell aggregation is cultured in a 20 mmol/L glucose medium for the last one hour and the secretion amount of insulin is measured in glucose at a high concentration. It is possible to produce a 20 mmol/L glucose medium by adding a glucose solution to a 3 mmol/L glucose-containing medium (manufactured by COSMO BIO co., ltd.: PNI14) using this medium as a medium. During measurement, 400 µL of a medium with each glucose concentration is added to a well of a cell container (such as 6.5 mm Transwell (registered trademark) with 5.0 µm Pore Polycarbonate Membrane Insert, Sterile (manufactured by Corning) in which a filter-attached insert becomes a set with a 24-well plate), 100 µL of a 3 mmol/L glucose-containing medium (manufactured by COSMO BIO co., ltd.: PNI14) containing five cell aggregations is washed with 1 mL of the same medium, and 100 µL of the above-described medium containing five cell aggregations is placed on the insert. The insert is moved every hour, 400 µL of the medium in the well after moving the insert is collected, and insulin is quantitatively determined through enzyme-linked immunosorbent assay (ELISA). In ELISA, it is possible to use Rat Insulin ELISA (manufactured by ALPCO).

The method for producing a composition of the present invention is not particularly limited. For example, it is possible to produce the composition of the present invention by mixing a predetermined number of spheroids with a predetermined number of pancreatic islets in a culture container containing a liquid medium and culturing the mixture as desired. As described above in the present specification, in a case where the composition of the present invention is a composition containing a plurality of pancreatic islets and a plurality of spheroids in a liquid medium, the pancreatic islets and the spheroids may form a cell aggregation in the liquid medium, may float in the liquid medium, or these states may coexist with each other. As the culture container used herein, a container formed of a low-adhesive cell material or a non-adhesive cell material is preferable and a container formed of polystyrene, polypropylene, polyethylene, glass, polycarbonate, or polyethylene terephthalate is more preferable. The shape of the bottom surface of a container is preferably a flat bottom shape, a U-shape, and a V-shape.

[Pancreatic Islet Transplantation Treatment Agent and Hypoglycemic Agent]

The composition or the kit of the present invention can be used as a pancreatic islet transplantation treatment agent or a hypoglycemic agent. That is, according to the present invention, a pancreatic islet transplantation treatment agent containing the composition or the kit of the present invention and a hypoglycemic agent containing the composition or the kit of the present invention are provided.

In a case of using the composition or the kit of the present invention as a pancreatic islet cell transplantation treatment agent, it is possible to administer these to a diabetic patient, a patient whose pancreas is completely removed, or the like. In a case of using the composition or the kit of the present invention as a hypoglycemic agent, for example, it is possible to administer these to a patient, such as an insulin-dependent diabetic patient and a patient whose pancreas is completely removed, who requires reduction in blood sugar and whose blood sugar is higher than a normal value.

As the transplantation method, it is possible to use a method using incision, injection, or an endoscope.

The transplantation site is not particularly limited and examples thereof include under the skin, within the liver, within the muscle, within the greater omentum, or under the renal capsule. However, in the case of using the present invention as a pancreatic islet transplantation treatment agent, it is preferable to transplant the present invention under the skin or into the muscle.

The number of pancreatic islets in the pancreatic islet transplantation treatment agent and the hypoglycemic agent of the present invention can be set to the number of pancreatic islets which has been calculated such that a desired treatment effect is produced. The number of pancreatic islets per administration of the pancreatic islet transplantation treatment agent and the hypoglycemic agent of the present invention can be appropriately set using the body weight of a patient, the degree of symptoms, or the like, and is generally about $1 \times 10^2$ to $1 \times 10^5$ pieces/kg body weight per 1 kg of the body weight of a patient.

According to the present invention, there is provided a pancreatic islet transplantation method including a step of transplanting the composition or the kit of the present invention into a patient who requires transplantation of a pancreatic islet. According to the present invention, there is provided a cell transplantation method including a step of transplanting the composition or the kit of the present invention into a patient who requires reduction in blood sugar.

According to the present invention, there is further provided use of the composition or the kit of the present invention for producing a pancreatic islet transplantation treatment agent. According to the present invention, there is provided use of the composition or the kit of the present invention for producing a hypoglycemic agent.

The present invention will be more specifically described using the following Examples, but is not limited by Examples.

EXAMPLES

Example A1

Recombinant Peptide (Recombinant Gelatin)

The following CBE3 (which is disclosed in WO2008/103041A) was prepared as recombinant peptides (recombinant gelatin).

CBE3:
Molecular weight: 51.6 kD
Structure: GAP[(GXY)$_{63}$]$_3$G
Number of amino acids: 571
RGD sequence: 12
Imino acid content: 33%

Almost 100% of amino acids have a repeating structure of GXY. In the amino acid sequence of CBE3, serine, threonine, asparagine, tyrosine, and cysteine are not included. CBE3 has an ERGD sequence.
Isoelectric point: 9.34
GRAVY value: −0.682
1/IOB value: 0.323

Amino acid sequence (SEQ ID No: 1 in a sequence table) (which is the same as that of SEQ ID No: 3 in WO2008/103041A. However, X in the end is corrected to "P").

GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)3G

Example A2

Production of Porous Body of Recombinant Peptide

[PTFE Thickness·Cylindrical Container]

A cylindrical cup-shaped polytetrafluoroethylene (PTFE) container with a bottom surface thickness of 3 mm, a diameter of 51 mm, a side surface thickness of 8 mm, and a height of 25 mm was prepared. When the curved surface of the cylindrical cup-shaped PTFE container is set as a side surface, the side surface is closed by PTFE with 8 mm and the bottom surface (circular shape of a flat plate) is also closed by PTFE with 3 mm. In contrast, the upper surface is in an open shape. Accordingly, the inner diameter of the cylindrical cup-shaped container is set to 43 mm. Hereinafter, this container is referred to as a PTFE thickness·cylindrical container.

An aqueous CBE3 solution was made to flow into a PTFE thickness·cylindrical container and was cooled down from the bottom surface within a vacuum freeze dryer (TF5-85ATNNN: manufactured by Takara Co., Ltd.) using a cooling shelf. The final concentration of the aqueous CBE3 solution was 4 mass % and the amount of aqueous solution was 8 mL. As the setting for the temperature of the shelf, the temperature was cooled down until the temperature reaches −10° C., and then, freezing was performed for 1 hour at −10° C., for 2 hours at −20° C., for 3 hours at −40° C., and finally for 1 hour at −50° C. Thereafter, the obtained frozen product was subjected to vacuum drying for 24 hours at −20° C. after the setting of the temperature of the shelf was returned to −20° C. After 24 hours, the temperature of the shelf was increased to 20° C. in a state in which the vacuum drying was continued as it was, and the vacuum drying was further performed for 48 hours at 20° C. until the vacuum degree was sufficiently decreased (1.9×10$^5$ Pa). Then, the product was taken out of the vacuum freeze dryer. A porous body was obtained as described above.

Since each of the aqueous solutions is cooled down from the bottom surface when producing porous bodies, it is most difficult for the temperature of the surface of water in the center portion of a circle to be cooled down. Accordingly, the portion of the surface of water in the center portion of the circle has the highest liquid temperature within the solution. Therefore, the liquid temperature of the portion of the surface of water in the center portion of the circle was measured. Hereinafter, the liquid temperature in the portion of the surface of water in the center portion of the circle is referred to as the highest internal liquid temperature.

Example A3

Measurement of Highest Internal Liquid Temperature in Freezing Step

Temperature profiles with respect to each of the conditions A, B, and C when freezing a solvent are shown in FIG. 1. The temperature started to increase due to generation of solidification heat after an unfrozen state at lower than or equal to a melting point, and ice formation actually started in this stage. Thereafter, the temperature was around 0° C. while the certain time passes. In this stage, the product was in a state where there was a mixture of water and ice. The temperature finally started to decrease again from 0° C. In this stage, the liquid portion became ice while being disappeared. The temperature being measured became a solid temperature within the ice, that is, was not the liquid temperature. As described above, whether or not the freezing was performed after the highest internal liquid temperature exceeds a "melting point of a solvent −3° C." in the unfrozen state can be found if the highest internal liquid temperature at the moment when solidification heat is generated is checked.

The highest internal liquid temperature in the unfrozen state at the moment when solidification heat was generated became −8.8° C. It can be seen that the highest internal liquid temperature is lower than or equal to the "melting point of a solvent −3° C." in the unfrozen state if the highest internal liquid temperature at the moment when solidification heat is generated is checked.

Example 4

Production of Recombinant Peptide Block (Pulverizing and Cross-Linking of Porous Body)

The CBE3 porous body which had been produced in Example A2 was pulverized using NEW POWERMILL (Osaka Chemical Co., Ltd., NEW POWERMILL PM-2005). The pulverizing was performed for one minute×5 times, that is, for 5 minutes in total at the maximum rotation speed. The size of the obtained pulverized substance was divided using a stainless steel sieve to obtain CBE3 blocks at 25 to 53 μm, 53 to 106 μm, and 106 μm to 180 μm in a granular form. Thereafter, recombinant peptide blocks were obtained by performing thermal cross-linking (performed for 8 to 48 hours of the cross-linking time) at 160° C. in nitrogen atmosphere. Hereinafter, blocks at 53 to 106 μm were used in all cases.

Example A5

Production of Cell Structure Using Recombinant Peptide Block (Rat Pancreatic Islet+Human Bone Marrow-derived Mesenchymal Stem Cells (hMSC))

The number of human bone marrow-derived mesenchymal stem cells (hMSC) which were cultured in a proliferation medium (manufactured by TAKARA BIO INC.:

MSCGM BulletKit™) was adjusted to 50000 cells/mL using a 3 mM glucose-containing medium (manufactured by COSMO BIO co., ltd.: PNI14), and the CBE3 blocks produced in Example A4 were added thereto so as to make a concentration of 0.1 mg/mL. 200 μL of this mixed liquid was sown in a Sumilon Celltight X96U plate (of which the bottom was in a U-shape and was manufactured by Sumitomo Bakelite Co., Ltd.), in which 10 rat pancreatic islets (manufactured by COSMO BIO co., ltd: PNI14) (an aggregate of an α cell, a β cell, a δ cell, an ε cell, and a PP cell) were placed, and the plate was centrifuged in Mini Plate Centrifuge (200 g, 5 minutes) and was allowed to stand for 24 hours to produce a cell structure which had a spherical shape with a diameter of about 1 mm and was formed of CBE3 blocks, hMSC, and rat pancreatic islets. Since the cell structure was produced in the U-shaped plate, the shape of this cell structure became spherical.

Comparative Example A1

Production of Cell Aggregations (Rat Pancreatic Islet)

10 rat pancreatic islets (manufactured by COSMO BIO co., ltd.: PNI14) were placed in a Sumilon Celltight X96U plate (of which the bottom was in a U-shape and which was manufactured by Sumitomo Bakelite Co., Ltd.) in which 200 μL of a 3 mM glucose-containing medium (manufactured by COSMO BIO co., ltd.: PNI14) was placed, and the plate was centrifuged in Mini Plate Centrifuge (200 g, 5 minutes) and was allowed to stand for 24 hours to produce a cell aggregation which had a spherical shape with a diameter of about 300 μm and was formed of rat pancreatic islets. Since the cell aggregation was produced in the U-shaped plate, the shape of this cell aggregation became spherical.

Comparative Example A2

Production of Cell Aggregations (Rat Pancreatic Islet+hMSC)

The number of human bone marrow-derived mesenchymal stem cells (hMSC) cultured in a proliferation medium (manufactured by TAKARA BIO INC.: MSCGM BulletKit™) was adjusted to 50000 cells/mL using a 3 mM glucose-containing medium (manufactured by COSMO BIO co., ltd.: PNI14). 200 μL of this cell suspension was sown in a Sumilon Celltight X96U plate (of which the bottom was in a U-shape and was manufactured by Sumitomo Bakelite Co., Ltd.), in which 10 rat pancreatic islets (manufactured by COSMO BIO co., ltd: PNI14) were placed, and the plate was centrifuged in Mini Plate Centrifuge (200 g, 5 minutes) and was allowed to stand for 24 hours to produce a cell aggregation which had a spherical shape with a diameter of about 500 μm and was formed of hMSC and rat pancreatic islets. Since the cell aggregation was produced in the U-shaped plate, the shape of this cell aggregation became spherical.

Comparative Example A3

Production of Block-Containing Cell Aggregation (Rat Pancreatic Islet+Block)

200 μL of a 3 mM glucose-containing medium (manufactured by COSMO BIO co., ltd.: PNI14) which was suspended such that the concentration of the CBE3 blocks produced in Example A4 became 0.1 mg/mL was sown in a Sumilon Celltight X96U plate (of which the bottom was in a U-shape and was manufactured by Sumitomo Bakelite Co., Ltd.), in which 10 rat pancreatic islets (manufactured by COSMO BIO co., ltd: PNI14) were placed, and the plate was centrifuged in Mini Plate Centrifuge (200 g, 5 minutes) and was allowed to stand for 24 hours to produce a cell aggregation formed of CBE3 blocks and rat pancreatic islets.

Example A6

Production of Cell Structure Using Recombinant Peptide Block (Rat Pancreatic Islet Cell+hMSC)

The number of pancreatic islet cells which were obtained by dispersing 10 rat pancreatic islets (manufactured by COSMO BIO co., ltd.: PNI14) using a cell dispersion liquid for pancreatic islets (manufactured by COSMO BIO co., ltd.: PNIDME) was adjusted to 50000 cells/mL using a 3 mM glucose-containing medium (manufactured by COSMO BIO co., ltd.: PNI14). Human bone marrow-derived mesenchymal stem cells (hMSC) cultured in a proliferation medium (TAKARA BIO INC.: MSCGM BulletKit™) were added thereto so as to make the number of cells be 50000 cells/mL and the CBE3 blocks produced in Example A4 were further added thereto so as to make a concentration of 0.1 mg/mL. 200 μL of this mixed liquid was sown in a Sumilon Celltight X96U plate (of which the bottom was in a U-shape and was manufactured by Sumitomo Bakelite Co., Ltd.), and the plate was centrifuged in Mini Plate Centrifuge (200 g, 5 minutes) and was allowed to stand for 24 hours to produce a cell structure which had a spherical shape with a diameter of about 1 mm and was formed of CBE3 blocks, hMSC, and rat pancreatic islet cells. Since the cell structure was produced in the U-shaped plate, the shape of this cell structure became spherical.

Comparative Example A4

Production of Cell Aggregation (Rat Pancreatic Islet Cell)

The number of pancreatic islet cells which were obtained by dispersing 10 rat pancreatic islets (manufactured by COSMO BIO co., ltd.: PNI14) using a cell dispersion liquid for pancreatic islets (manufactured by COSMO BIO co., ltd.: PNIDME) was adjusted to 50000 cells/mL using a 3 mM glucose-containing medium (manufactured by COSMO BIO co., ltd.: PNI14). 200 μL of this cell suspension was sown in a Sumilon Celltight X96U plate (of which the bottom was in a U-shape and was manufactured by Sumitomo Bakelite Co., Ltd.), and the plate was centrifuged in Mini Plate Centrifuge (200 g, 5 minutes) and was allowed to stand for 24 hours to produce a cell aggregation which had a spherical shape with a diameter of about 300 μm and was formed of rat pancreatic islet cells. Since the cell structure was produced in the U-shaped plate, the shape of this cell structure became spherical.

Comparative Example A5

Production of Cell Aggregation (Rat Pancreatic Islet Cells+hMSC)

The number of pancreatic islet cells which were obtained by dispersing 10 rat pancreatic islets (manufactured by COSMO BIO co., ltd.: PNI14) using a cell dispersion liquid for pancreatic islets (manufactured by COSMO BIO co., ltd.: PNIDME) was adjusted to 50000 cells/mL using a 3 mM glucose-containing medium (manufactured by COSMO BIO co., ltd.: PNI14). Human bone marrow-derived mesenchymal stem cells (hMSC) cultured in a proliferation medium (manufactured by TAKARA BIO INC.: MSCGM BulletKit™) were added to this cell suspension so as to make the number of cells be 50000 cells/mL. 200 μL of this cell suspension was sown in a Sumilon Celltight X96U plate (of which the bottom was in a U-shape and was manufactured by Sumitomo Bakelite Co., Ltd.), and the plate was centrifuged in Mini Plate Centrifuge (200 g, 5 minutes) and was allowed to stand for 24 hours to produce a cell aggregation which had a spherical shape with a diameter of about 500 μm and was formed of hMSC and rat pancreatic islets. Since the cell aggregation was produced in the U-shaped plate, the shape of this cell aggregation became spherical.

Comparative Example A6

Production of Block-Containing Cell Aggregation (Rat Pancreatic Islet Cell+Block)

The number of pancreatic islet cells which were obtained by dispersing 10 rat pancreatic islets (manufactured by COSMO BIO co., ltd.: PNI14) using a cell dispersion liquid for pancreatic islets (manufactured by COSMO BIO co., ltd.: PNIDME) was adjusted to 100000 cells/mL using a 3 mM glucose-containing medium (manufactured by COSMO BIO co., ltd.: PNI14). The CBE3 blocks produced in Example A4 were added to this cell suspension so as to make a concentration of 0.0375 mg/mL, 200 μL of this suspension was sown in a Sumilon Celltight X96U plate (of which the bottom was in a U-shape and was manufactured by Sumitomo Bakelite Co., Ltd.), and the plate was centrifuged in Mini Plate Centrifuge (200 g, 5 minutes) and was allowed to stand for 24 hours to produce a cell aggregation formed of CBE3 blocks and rat pancreatic islet cells.

Example A7

In Vitro Glucose Sensitivity Test

Regarding the cell structures produced in Examples A5 and A6 and the cell aggregations produced in Comparative Examples A1 to A6, the presence or absence of glucose sensitivity in which insulin was secreted in accordance with the concentration of glucose was checked. The above-described cell structures and the above-described cell aggregations which had been cultured for seven days were transferred to media, which had different glucose concentrations, every hour, and each amount of insulin in the media was calculated.

The process was performed for three hours in total. The secretion amount of insulin was stabilized in a 3 mM glucose medium during the first one hour, the secretion amount of insulin in glucose at a low concentration was measured in a 3 mM glucose medium for the next one hour, and the secretion amount of insulin in glucose at a high concentration was measured in a 20 mM glucose medium for the next one hour. The 20 mM glucose medium was produced as a medium using a 3 mM glucose-containing medium (manufactured by COSMO BIO co., ltd.: PNI14) after adding a glucose solution to the medium.

During the measurement, 6.5 mm Transwell (registered trademark) with 5.0 μm Pore Polycarbonate Membrane Insert, Sterile (manufactured by Corning) in which a filter-attached insert became a set with a 24-well plate was used.

First, 400 μL of a medium with each glucose concentration was added to each well. 100 μL of a 3 mM glucose-containing medium (manufactured by COSMO BIO co., ltd.: PNI14) which contained five cell structures produced in Examples A5 and A6 and five cell aggregations produced in Comparative Examples A1 to A6 was washed in 1 ml of the same medium. 100 μL of the same medium which contained five cell structures produced in Examples A5 and A6 and five cell aggregations produced in Comparative Examples A1 to A6 was placed on the insert.

The insert was moved every hour, 400 μL of the medium in the well after moving the insert was collected, and insulin was quantitatively determined through ELISA. Rat Insulin ELISA (manufactured by ALPCO) was used in ELISA. The amount of insulin during culture in the second 3 mM glucose medium and the amount of insulin during culture in the 20 mM glucose medium were obtained and each SI value (SI=amount of insulin during culture in 20 mM glucose medium/amount of insulin during culture in 3 mM glucose medium) was calculated as an index of the glucose sensitivity.

As a result, SI in the pancreatic islet cell aggregation in Comparative Example A1 was 1.21, SI in the pancreatic islet+hMSC cell aggregation in Comparative Example A2 was 2.00, and SI in Comparative Example A3 was 0.99, whereas SI in the pancreatic islet+hMSC cell structure produced in Example A5 was 3.12. In contrast, SI in the pancreatic islet cell aggregation in Comparative Example A4 was 1.23, SI in the pancreatic islet cell+hMSC cell aggregation in Comparative Example A5 was 2.93, and SI in Comparative Example A6 was 0.85, whereas SI in the pancreatic islet cell+hMSC cell structure in Example A6 was 3.59 (Table 1).

From these results, in all of the pancreatic islets and the dispersed pancreatic islet cells, it became clear that SI was slightly increased in a case where only MSC was added and SI became highest in the case of cell structure in which both CBE3 blocks and MSC were mixed in, whereas SI was decreased in a case where only CBE3 was added. That is, it was possible to improve glucose sensitivity by culturing CBE3 blocks and MSC together with pancreatic islets or pancreatic islet cells.

TABLE 1

Summary of Examples A5 and A6 and Comparative Examples A1 to A6

|  | Configuration | Glucose sensitivity (SI) |
|---|---|---|
| Example A5 | Rat pancreatic islet + hMSC + macromolecular block | 3.12 |
| Comparative Example A1 | Rat pancreatic islet | 1.21 |
| Comparative Example A2 | Rat pancreatic islet + hMSC | 2.00 |
| Comparative Example A3 | Rat pancreatic islet + macromolecular block | 0.99 |
| Example A6 | Rat pancreatic islet cell + hMSC + macromolecular block | 3.59 |
| Comparative Example A4 | Rat pancreatic islet cell | 1.23 |
| Comparative Example A5 | Rat pancreatic islet cell + hMSC | 2.93 |
| Comparative Example A6 | Rat pancreatic islet cell + macromolecular block | 0.85 |

Example A8

Production of Cell Structure Using Recombinant Peptide Block for Transplantation (hMSC)

The number of human bone marrow-derived mesenchymal stem cells (hMSC) was adjusted to 2500 cells/mL using a proliferation medium (manufactured by TAKARA BIO INC.: MSCGM BulletKit™), and the CBE3 blocks produced in Example A4 were added thereto so as to make a concentration of 0.0025 mg/mL. Then, 200 µL of the mixture was sown in a Sumilon Celltight X96U plate (of which the bottom was in a U-shape and was manufactured by Sumitomo Bakelite Co., Ltd.), and the plate was centrifuged in Mini Plate Centrifuge (600 g, 5 minutes) and was allowed to stand for 24 hours to produce a cell structure which had a spherical shape with a diameter of about 200 µm and was formed of CBE3 blocks and hMSC cells. Since the cell structure was produced in the U-shaped plate, the shape of this cell structure became spherical. In addition, the size of the cell structure was the same as that of a pancreatic islet.

Comparative Example A7

Production of Cell Aggregation for Transplantation (hMSC)

The number of human bone marrow-derived mesenchymal stem cells (hMSC) was adjusted to 2500 cells/mL using a proliferation medium (manufactured by TAKARA BIO INC.: MSCGM BulletKit™), 200 µL of the mixture was sown in a Sumilon Celltight X96U plate (of which the bottom was in a U-shape and was manufactured by Sumitomo Bakelite Co., Ltd.), and the plate was centrifuged in Mini Plate Centrifuge (600 g, 5 minutes) and was allowed to stand for 24 hours to produce a cell aggregation which had a spherical shape with a diameter of about 200 µm and was formed of hMSC cells. Since the cell aggregation was produced in the U-shaped plate, the shape of this cell aggregation became spherical. In addition, the size of the cell aggregation was the same as that of a pancreatic islet.

Example A9

Production of Diabetic Mouse and Measurement of Blood Sugar Level

A diabetic mouse whose blood sugar level was increased was prepared in order to check an effect of pancreatic islets to be transplanted.

Male mice at the age of 6 weeks of NOD/SCID (manufactured by Charles River Laboratories International) were used as mice. First, 200 mg/kg of STREPTOZOTOCIN (manufactured by Wako Pure Chemical Industries, Ltd.) was administered to the mice. The blood sugar levels were measured after three days and seven days of the administration, and a mouse whose blood sugar levels of all of the cases were greater than or equal to 300 mg/dl was set as a diabetic mouse. Venous blood was collected from the caudal vein of the mouse using a 28 G injection needle, and the blood sugar level was measured using a glucose concentration measuring device GLUCOSE PILOT (manufactured by IWAI CHEMICALS COMPANY).

Example A10

Subcutaneous Transplantation of Cell Structure, Cell Aggregation, and Pancreatic Islet into Diabetic Mouse A diabetic mouse after seven days of administration of STREPTOZOTOCIN which was prepared in Example A9 was used for transplantation. Body hair of the back of the diabetic mouse was removed under anesthesia and the transplantation was performed through each of the following methods. Regarding (1) to (6), a 18 G injection needle was inserted under the skin of the back and an end of a 200 µL scale tip was attached to an injection port of the injection needle. Three types of the following transplantation substances were previously placed in the tip through inhalation using a pipette, and the transplantation substances were gathered at a distal end of the tip. After attaching the tip to the injection needle, a dial of the pipette was turned to subcutaneously inject the transplantation substances together with 100 µL of a medium. Regarding (7), after subcutaneously incising the back, ten cell aggregations placed on a spatula were placed under the skin of a lower part approximately 1 cm away from the cut portion which was then sutured. After the transplantation, the blood sugar level was measured every three days to four days.

The transplantation substances in (1) to (6) were transplantation substances obtained by mixing three types of the following in a 3 mM glucose-containing medium (manufactured by COSMO BIO co., ltd.: PNI14).

A transplantation substance in (7) was a substance obtained by culturing (3) before transplantation to make an aggregation.

(1) 200 pancreatic islets (manufactured by COSMO BIO co., ltd.: PNI14) (which are an aggregate of an α cell, a β cell, a δ cell, an ε cell, and a PP cell)

(2) 400 hMSC cell aggregations (Comparative Example A7)+200 pancreatic islets (manufactured by COSMO BIO co., ltd.: PNI14) (which are an aggregate of an α cell, a β cell, a δ cell, an ε cell, and a PP cell)

(3) 400 hMSC cell structures (Example A8)+200 pancreatic islets (manufactured by COSMO BIO co., ltd.: PNI14) (which are an aggregate of an α cell, a β cell, a δ cell, an ε cell, and a PP cell)

(4) 400 pancreatic islets (manufactured by COSMO BIO co., ltd.: PNI14) (which are an aggregate of an α cell, a β cell, a δ cell, an ε cell, and a PP cell)

(5) 800 hMSC cell aggregations (Comparative Example A7)+400 pancreatic islets (manufactured by COSMO BIO co., ltd.: PNI14) (which are an aggregate of an α cell, a β cell, a δ cell, an ε cell, and a PP cell)

(6) 800 hMSC cell structures (Example A8)+400 pancreatic islets (manufactured by COSMO BIO co., ltd.: PNI14) (which are an aggregate of an α cell, a β cell, a δ cell, an ε cell, and a PP cell)

(7) 400 hMSC cell structures (Example A8)+200 pancreatic islets (manufactured by COSMO BIO co., ltd.: PNI14) (which are an aggregate of an α cell, a β cell, a δ cell, an ε cell, and a PP cell)

However, 10 aggregations which were produced by culturing 40 hMSC cell structures (Example A8)+20 pancreatic islets (manufactured by COSMO BIO co., ltd.: PNI14) (which were an aggregate of an α cell, a β cell, a δ cell, an ε cell, and a PP cell) in 200 µL of a 3 mM glucose-containing medium (manufactured by COSMO BIO co., ltd.: PNI14) for 2.5 hours using a Sumilon Celltight X96U plate (of which the bottom was in a U-shape and was manufactured by Sumitomo Bakelite Co., Ltd.)

Figure 2:
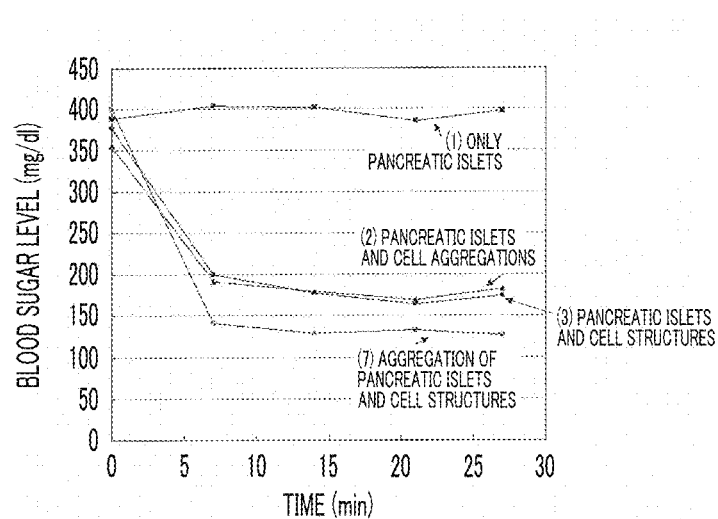
FIG. 2 shows results obtained by measuring blood sugar levels after subcutaneously transplanting pancreatic islet with cell structures and cell aggregations into a diabetic mouse.

The results are shown in FIG. 2. The blood sugar level after four weeks of transplantation in the case of (1) in which only 200 pancreatic islets were transplanted was 398 mg/dl which remained high. However, the blood sugar level in the case of (2) in which a mixture of cell aggregations and 200 pancreatic islets was transplanted was 183 mg/dl and the blood sugar level in the case of (3) in which a mixture of cell structures and 200 pancreatic islets was transplanted was 174 mg/dl, that is, it was possible to decrease the blood sugar level up to a normal value. Furthermore, the blood sugar level in a case where transplantation was performed after performing culture through the method of (7) was 127 mg/dl, that is, it was possible to further decrease the blood sugar level up to a completely normal value. Accordingly, it became clear that the blood sugar level can be decreased in a case where both pancreatic islets and hMSC cell structures containing CBE3 blocks were transplanted, whereas the blood sugar level cannot be decreased using only 200 pancreatic islets in a case where the pancreatic islets were transplanted. Furthermore, it was found that the blood sugar level can be further decreased up to a normal value by performing culture before transplantation to make an aggregation.

Example A11

Verification of Ability to Normalize Blood Sugar Level in Glucose Tolerance Test A glucose tolerance test was performed in order to verify how much a mouse has an ability to return the blood sugar level to a normal value when sugar is loaded. Tests were performed on mice into which (1) to (7) were transplanted after four weeks of transplantation. First, the mice were made to be in a fasting condition for 20 hours, and the blood sugar levels were measured. Thereafter, 2 mg/g of glucose was intraperitoneally injected to a mouse per body weight. The blood sugar levels were measured after the injection, after 15 minutes, after 30 minutes, after 45 minutes, after 60 minutes, after 90 minutes, after 120 minutes, and after 180 minutes. The same tests were performed even on a diabetic mouse into which transplantation was not performed and on a normal mouse into which STREPTOZOTOCIN was not administered.

Figure 3:
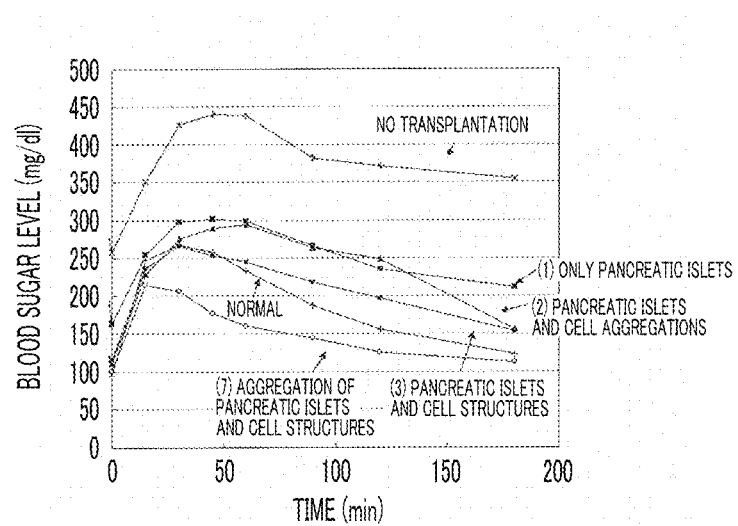
FIG. 3 shows results of verification (in a case of 200 pancreatic islets) of an ability to normalize a blood sugar level in a glucose tolerance test.
Figure 4:
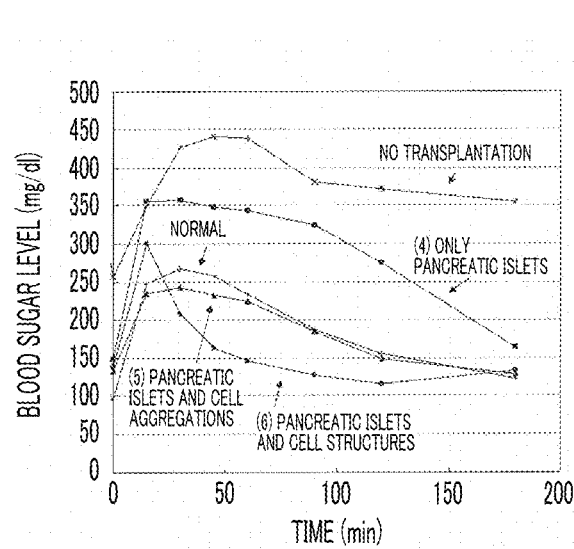
FIG. 4 shows results of verification (in a case of 400 pancreatic islets) of an ability to normalize a blood sugar level in a glucose tolerance test.

The results are shown in FIGS. 3 and 4. FIG. 3 shows results of (1) to (3) and (7) in a case of 200 pancreatic islets and FIG. 4 shows results of (4) to (6) in a case of 400 pancreatic islets.

In the case of 200 pancreatic islets, although the condition of the blood sugar level was not as high as that of the mouse, into which transplantation was not performed, in the case of (1) in which only 200 pancreatic islets were transplanted, it resulted that the blood sugar level was hard to decrease compared to that of a normal mouse. In contrast, in the case of (2) in which a mixture of cell aggregations and 200 pancreatic islets was transplanted, it was possible to decrease the blood sugar level compared to the case of (1) in which only the pancreatic islets were used. Furthermore, in the case of (3) in which a mixture of cell structures and 200 pancreatic islets was transplanted, it resulted that the same ability to decrease blood sugar as that of a normal mouse was exhibited and almost the same curve as that of a normal mouse was drawn. Furthermore, it was found that, in the case of (7) in which cell structures which were transplanted using aggregations after culture were transplanted, it was shifted that the blood sugar level was lower than that of a normal mouse and an ability to return the blood sugar level to a normal state was higher than that of a normal mouse.

Similarly in the case of 400 pancreatic islets, although the condition of the blood sugar level was not as high as that of the mouse, into which transplantation was not performed, in the case of (4) in which only pancreatic islets were transplanted, it resulted that the blood sugar level was hard to decrease compared to that of a normal mouse. In contrast, it can be seen that, in the case of (5) in which cell aggregations and pancreatic islets were transplanted, the same transition as that of a normal mouse was shown and the blood sugar level was easily decreased. Furthermore, in the case of (6) in which a mixture of cell structures and pancreatic islets was transplanted, although the blood sugar level was increased immediately after the glucose injection, it was possible to decrease the blood sugar level to a normal value, and therefore, transition of a lower blood sugar level than that of a normal mouse was shown.

In addition, the area of a lower portion of a curve of a graph was obtained regarding each of the graphs. The area was calculated after dividing the graphs for each measurement time and adding a result of time (min)×blood sugar level (mg/dl). It can be said that the smaller the area is, the higher the ability to normalize the blood sugar level is.

The area of each lower portion was 45614 min·mg/dl for (1), 43104 min·mg/dl for (2), 37682 min·mg/dl for (3), 51795 min·mg/dl for (4), 32752 min·mg/dl for (5), 27405 min·mg/dl for (6), and 26658 min·mg/dl for (7).

From these results, it was possible to confirm that, in either pattern of 200 pancreatic islets or 400 pancreatic islets, the case where both pancreatic islets and hMSC cell structures containing CBE3 blocks were transplanted had a high ability to normalize the blood sugar level, compared to the case where only pancreatic islets were transplanted or the case where pancreatic islets and hMSC cell aggregations were transplanted. In addition, it was found that it was possible to more efficiently decrease the blood sugar level by culturing pancreatic islets and cell structures before transplantation to make an aggregation.

The above-described results are summarized in Table 2.

TABLE 2

|  | Vitro SI | 200 pancreatic islets in vivo | | 400 pancreatic islets in vivo |
|---|---|---|---|---|
|  |  | Blood sugar level (mg/dl) on day 28 | AUC (min mg/dl) in glucose tolerance test | AUC (min mg/dl) in glucose tolerance test |
| Only pancreatic islets | 1.21 | 398 | 45614 | 51795 |
| Pancreatic islets + cell aggregations | 2 | 183 | 43104 | 32752 |
| Pancreatic islets + cell structures | 3.12 | 174 (127) | 37682 (26658) | 27405 |

(The numerical values in parentheses are the results in a case where aggregations were made by culturing the pancreatic islets and cell structures)

Example A12

Measurement of Concentration of C-Peptide in Blood Sample Serum

In order to quantitatively determine how much transplanted pancreatic islets secreted insulin, quantitative determination was performed on c-peptide which produces the same molecular weight during the secretion of insulin.

A mouse after one week of transplantation was anesthetized and venous blood was collected from the vena cava. This blood was allowed to stand on ice for 30 minutes and was centrifuged by 1000 g×20 minutes, and supernatant blood serum was collected. The concentration of c-peptide of the blood serum was measured later using Rat c-peptide ELISA (manufactured by ALPCO).

As a result, the concentration of c-peptide shows a high value which is 86 pM in the case of (3) in which a mixture of cell structures and pancreatic islets is transplanted, whereas the concentration of c-peptide is low which is 51 pM in the case of (1) in which only pancreatic islets are transplanted and is 44 pM in the case of (2) in which a mixture of cell aggregations and pancreatic islets is transplanted. Accordingly, it became obvious that the blood sugar level can be decreased due to large secretion amount of insulin from pancreatic islets in the case where the pancreatic islets were transplanted together with hMSC cell structures containing CBE3 blocks. That is, in pancreatic islets in (3), it became clear that the blood sugar level can be decreased since glucose sensitivity, which referred to as production of a large amount of insulin in accordance with a high glucose concentration in blood, was high.

Example A13

Collection of Cell Structure and Analysis of Sample

Dissection was performed four weeks after the transplantation. The skin of the back was peeled off and the skin of the transplantation site was collected.

Tissue pieces with respect to the skin to which a transplantation substance was adhered was produced. The tissue was immersed in a 10 mass % formalin buffer solution, and formalin fixation was performed. Then, the tissue was embedded by paraffin, and tissue pieces of the skin containing the transplantation substance were produced. The pieces were subjected to Hematoxylin-Eosin stain (HE stain) and insulin immunostain using an anti-insulin antibody (Monoclonal Anti-Insulin antibody (manufactured by Sigma-Aldrich Co. LLC.: 12018)).

Figure 5:
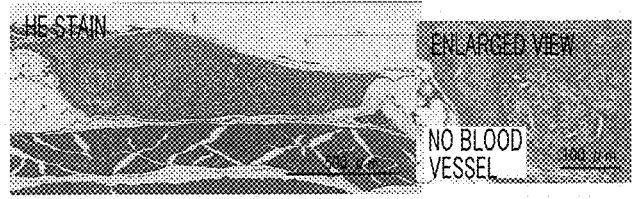
FIG. 5 shows tissue piece images after 4 weeks of subcutaneous transplantation performed on a diabetic mouse. An upper portion indicates Hematoxylin-Eosin stain (HE stain) and a lower portion indicates insulin immunostain.
Figure 5:
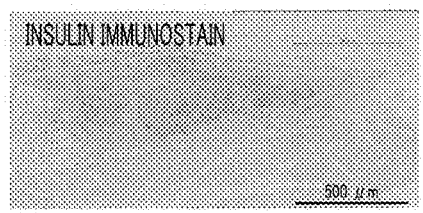
Figure 5:
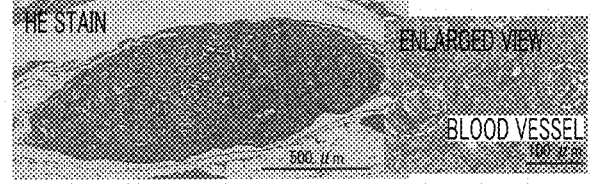
Figure 5:
Figure 5:
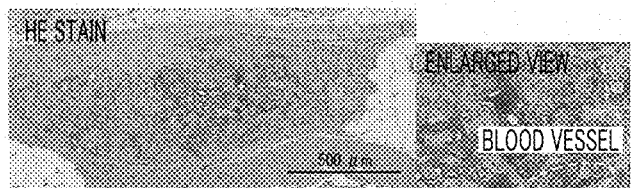
Figure 5:
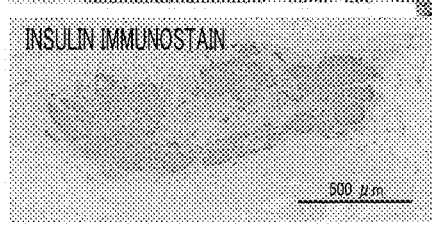

The results are shown in FIG. 5. In the case of (1) in which only pancreatic islets were transplanted, it was possible to check the transplanted pancreatic islets in a piece, and therefore, it was considered that the pancreatic islets were not taken. In the case of (2) in which a mixture of cell aggregations and pancreatic islets was transplanted, it was possible to check the transplanted pancreatic islets in a piece, but the amount of pancreatic islets which can be checked was small. Even in insulin immunostain, a stained region was small. In contrast, in the case of (3) in which a mixture of cell structures and pancreatic islets was transplanted, it was possible to check many pancreatic islets, which had been transplanted, in a piece, and the pancreatic islets were stained even through insulin immunostain. Furthermore, there were many blood vessels formed in a transplanted substance. This was a phenomenon which cannot be seen in the case of (2) in which a mixture of cell aggregations and pancreatic islets was transplanted. In the case of (7) in which aggregations which were made by culturing cell structures and pancreatic islets before transplantation were transplanted, it was possible to check many pancreatic islets which had been transplanted, there were many regions which were stained even through insulin immunostain, and there were many blood vessels formed in a transplantation substance.

Example B1

Production of hMSC Spheroid

The number of human bone marrow-derived mesenchymal stem cells (hMSC) was adjusted to 2500 cells/mL using a proliferation medium (manufactured by TAKARA BIO INC.: MSCGM BulletKit (registered trademark)), 200 μL of this cell suspension was sown in a Sumilon Celltight X96U plate (of which the bottom was in a U-shape and was manufactured by Sumitomo Bakelite Co., Ltd.), and the plate was centrifuged in Mini Plate Centrifuge (600 g, 5 minutes) and was allowed to stand for 24 hours to produce a hMSC spheroid which had a spherical shape with a diameter of about 200 μm. Since the hMSC spheroid was produced in the U-shaped plate, the shape of the obtained hMSC spheroid became spherical. In addition, the size of the hMSC spheroid was the same as that of a pancreatic islet.

Example B2

Production of Cell Aggregation of Pancreatic Islet and hMSC Spheroid 20 hMSC spheroids of Example B1 which had been cultured for one day and ten rat pancreatic islets (manufactured by COSMO BIO co., ltd.: PNI14) (an aggregate of an α cell, a β cell, a δ cell, an ε cell, and a PP cell) were mixed and cultured in a Sumilon Celltight X96U plate (of which the bottom was in a U-shape and was manufactured by Sumitomo Bakelite Co., Ltd.) in which 200 μL of a 3 mmol/L glucose-containing medium (manufactured by COSMO BIO co., ltd.: PNI14). As a result, a cell aggregation (one piece) of pancreatic islets and hMSC spheroids was produced.

Comparative Example B1

Production of Cell Aggregation (Rat Pancreatic Islet+hMSC)

The number of human bone marrow-derived mesenchymal stem cells (hMSC) which were cultured in a proliferation medium (manufactured by TAKARA BIO INC.: MSCGM BulletKit (registered trademark)) was adjusted to 50000 cells/mL using a 3 mmol/L glucose-containing medium (manufactured by COSMO BIO co., ltd.: PNI14). 200 μL of this cell suspension was sown in a Sumilon Celltight X96U plate (of which the bottom was in a U-shape and was manufactured by Sumitomo Bakelite Co., Ltd.) in which ten rat pancreatic islets (manufactured by COSMO BIO co., ltd.: PNI14) were placed, and the plate was centrifuged in Mini Plate Centrifuge (200 g, 5 minutes) and was allowed to stand for 24 hours to produce a cell aggregation formed of hMSC and rat pancreatic islets which had a spherical shape with a diameter of about 500 μm. Since the cell aggregation was produced in the U-shaped plate, the shape of the obtained cell aggregation became spherical.

Example B3

In Vitro Glucose Sensitivity Test

Regarding the cell aggregations produced in Example B2 and Comparative Example B1, the presence or absence of glucose sensitivity in which insulin was secreted in accordance with the concentration of glucose was checked. The above-described cell aggregations which had been cultured for one day were transferred to media, which had different glucose concentrations, every hour, and each amount of insulin in the media was calculated.

The process was performed for three hours in total. The secretion amount of insulin was stabilized in a 3 mmol/L glucose medium during the first one hour, the secretion amount of insulin in glucose at a low concentration was measured in a 3 mmol/L glucose medium for the next one hour, and the secretion amount of insulin in glucose at a high concentration was measured in a 20 mmol/L glucose medium for the next one hour. The 20 mmol/L glucose medium was produced as a medium using a 3 mmol/L glucose-containing medium (manufactured by COSMO BIO co., ltd.: PNI14) after adding a glucose solution to the medium.

During the measurement, 6.5 mm Transwell (registered trademark) with 5.0 μm Pore Polycarbonate Membrane Insert, Sterile (manufactured by Corning) in which a filter-attached insert became a set with a 24-well plate was used. First, 400 μL of a medium with each glucose concentration was added to each well. 100 μL of a 3 mmol/L glucose-containing medium (manufactured by COSMO BIO co., ltd.: PNI14) which contained one of the cell aggregations produced in Example B2 and Comparative Example B1 was washed in 1 mL of the same medium. 100 μL of the same medium which contained each one of the cell aggregations produced in Example B2 and Comparative Example B1 was placed on the insert.

The insert was moved every hour, 400 μL of the medium in the well after moving the insert was collected, and insulin was quantitatively determined through ELISA. Rat Insulin ELISA (manufactured by ALPCO) was used in ELISA. The amount of insulin during culture in the second 3 mmol/L glucose medium and the amount of insulin during culture in the 20 mmol/L glucose medium were obtained and each SI value (SI=amount of insulin during culture in 20 mmol/L glucose medium/amount of insulin during culture in 3 mmol/L glucose medium) was calculated as an index of the glucose sensitivity.

As a result, SI in the pancreatic islet+hMSC cell aggregation in Comparative Example B1 was 1.41, whereas SI in the cell aggregation of pancreatic islets+hMSC spheroids in Example B2 was 2.04.

From these results, it was found that hMSC can more improve glucose sensitivity of the pancreas in a spheroid state than a suspension state in a case where hMSC and pancreatic islets were cultured together.

Example B4

Preparation of Diabetic Mouse and Measurement of Blood Sugar Level

A diabetic mouse whose blood sugar level was increased was prepared in order to check an effect of pancreatic islets to be transplanted.

Male mice at the age of 6 weeks of Non Obese Diabetes/Severe Combined Immunodeficiency (NOD/SCID) (manufactured by Charles River Laboratories International) were used as mice. First, 200 mg/kg of STREPTOZOTOCIN (manufactured by Wako Pure Chemical Industries, Ltd.) was administered to the mice. The blood sugar levels were measured after three days and seven days of the administration, and a mouse whose blood sugar levels of all of the cases were greater than or equal to 300 mg/dl (300 mg/100 ml) was set as a diabetic mouse. Venous blood was collected from the caudal vein of the mouse using a 28 G injection needle, and the blood sugar level was measured using a glucose concentration measuring device GLUCOSE PILOT (manufactured by IWAI CHEMICALS COMPANY).

Comparative Example B2

Production of hMSC Cell Suspension

The number of human bone marrow-derived mesenchymal stem cells (hMSC) which were cultured in a proliferation medium (manufactured by TAKARA BIO INC.: MSCGM BulletKit (registered trademark)) was adjusted to 2000000 cells/mL and 4000000 cells/mL using a 3 mmol/L glucose-containing medium (manufactured by COSMO BIO co., ltd.: PNI14). 100 μL of this cell suspension was used for a transplantation test below.

Example B5

Subcutaneous Transplantation of Cell Aggregation and Pancreatic Islet into Diabetic Mouse The diabetic mouse after seven days of administration of STREPTOZOTOCIN which was prepared in Example B4 was used for transplantation. Body hair of the back of the diabetic mouse was removed under anesthesia, a 18 G injection needle was inserted under the skin of the back, and an end of a 200 μL scale tip was attached to an injection port of the injection needle. Two types of the following transplantation substances were previously placed in the tip through inhalation using a pipette, and the transplantation substances were gathered at a distal end of the tip. After attaching the tip to the injection needle, a dial of the pipette was turned to subcutaneously inject the transplantation substances together with 100 μL of a medium. After the transplantation, the blood sugar level was measured every three days to four days. Venous blood was collected from the caudal vein of the mouse using a 28 G injection needle, and the blood sugar level was measured using a glucose concentration measuring device GLUCOSE PILOT (manufactured by IWAI CHEMICALS COMPANY).

The transplantation substances were transplantation substances obtained by mixing six types of the following in 100 μL of a 3 mmol/L glucose-containing medium (manufactured by COSMO BIO co., ltd.: PNI14). In (1) and (3), pancreatic islets are in a state of floating in a 3 mmol/L glucose-containing medium. In (2) and (4), hMSC spheroids and pancreatic islets are in a state of floating in a 3 mmol/L glucose-containing medium. In (5) and (6), hMSC and pancreatic islets are in a state of floating in a 3 mmol/L glucose-containing medium.

(1) 200 pancreatic islets (manufactured by COSMO BIO co., ltd.: PNI14) (which are an aggregate of an α cell, a β cell, a δ cell, an ε cell, and a PP cell)

(2) 400 hMSC spheroids (Example B1)+200 pancreatic islets (manufactured by COSMO BIO co., ltd.: PNI14) (which are an aggregate of an α cell, a β cell, a δ cell, an ε cell, and a PP cell)

(3) 400 pancreatic islets (manufactured by COSMO BIO co., ltd.: PNI14) (which are an aggregate of an α cell, a β cell, a δ cell, an ε cell, and a PP cell)

(4) 800 hMSC spheroids (Example B1)+400 pancreatic islets (manufactured by COSMO BIO co., ltd.: PNI14) (which are an aggregate of an α cell, a β cell, a δ cell, an ε cell, and a PP cell)

(5) 200000 hMSC cells (2000000 cells/mL of cells in Comparative Example B2 are prepared by 100 μL)+200 pancreatic islets (manufactured by COSMO BIO co., ltd.: PNI14) (which are an aggregate of an α cell, a β cell, a δ cell, an ε cell, and a PP cell)

(6) 400000 hMSC cells (4000000 cells/mL of cells in Comparative Example B2 are prepared by 100 μL)+400 pancreatic islets (manufactured by COSMO BIO co., ltd.: PNI14) (which are an aggregate of an α cell, a β cell, a δ cell, an ε cell, and a PP cell)

Figure 6:
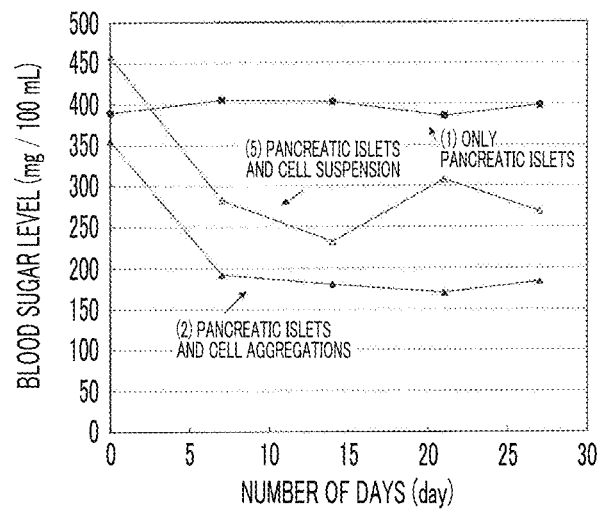
FIG. 6 shows blood sugar levels after transplantation of 200 pancreatic islets.

Results obtained by measuring the blood sugar levels after transplanting the above-described (1), (2), and (5) were shown in FIG. 6. The blood sugar level after four weeks of transplantation in the case of (1) in which only 200 pancreatic islets were transplanted was 398 mg/dl which remained high. However, the blood sugar level in the case of (5) in which a cell suspension and pancreatic islets were transplanted was 268 mg/dl and the blood sugar level in the case of (2) in which a mixture of hMSC spheroids and 200 pancreatic islets was transplanted was 183 mg/dl, that is, it was possible to decrease the blood sugar level up to a normal value. Accordingly, the blood sugar level can be decreased in a case where both hMSC and pancreatic islets were transplanted, compared to the case of using only pancreatic islets, whereas the blood sugar level cannot be decreased using only 200 pancreatic islets in a case where the 200 pancreatic islets were transplanted. Furthermore, it was possible to confirm that the blood sugar level can be further decreased up to a normal value by making hMSC into a spheroid and transplanting the spheroid.

Example B6

Verification of Ability to Normalize Blood Sugar Level in Glucose Tolerance Test A glucose tolerance test was performed in order to verify how much a mouse has an ability to return the blood sugar level to a normal value when sugar is loaded. Tests were performed on mice into which (1) to (6) were transplanted after four weeks of transplantation. First, the mice were made to be in a fasting condition for 20 hours, and the blood sugar levels were measured. Thereafter, 2 mg/g of glucose was intraperitoneally injected to a mouse per body weight. The blood sugar levels were measured after the injection, after 15 minutes, after 30 minutes, after 45 minutes, after 60 minutes, after 90 minutes, after 120 minutes, and after 180 minutes. The same tests were performed even on a diabetic mouse into which transplantation was not performed and on a normal mouse into which STREPTOZOTOCIN was not administered.

Transition of each blood sugar level was made into a graph, and the area of a lower portion of a curve (Area Under Curve: AUC) of the graph was obtained. The area was calculated after dividing the graph for each measurement time and adding a result of time (min)×blood sugar level (mg/dl). It can be said that the smaller the area is, the higher the ability to normalize the blood sugar level is.

Figure 7:
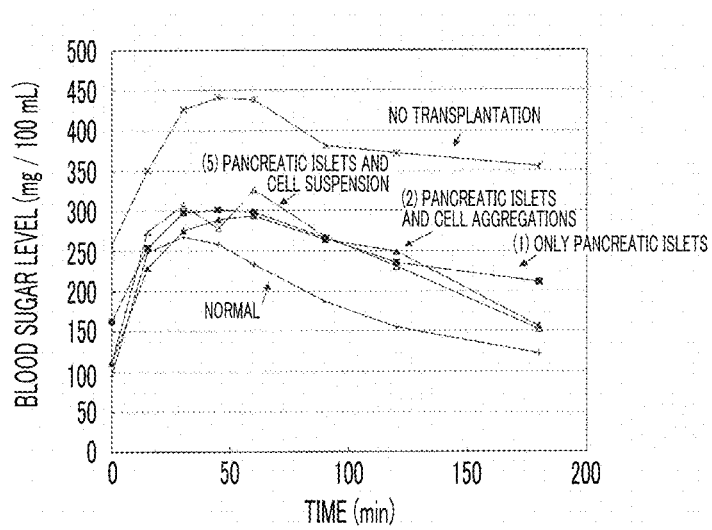
FIG. 7 shows results of glucose tolerance tests of 200 pancreatic islets.
Figure 8:
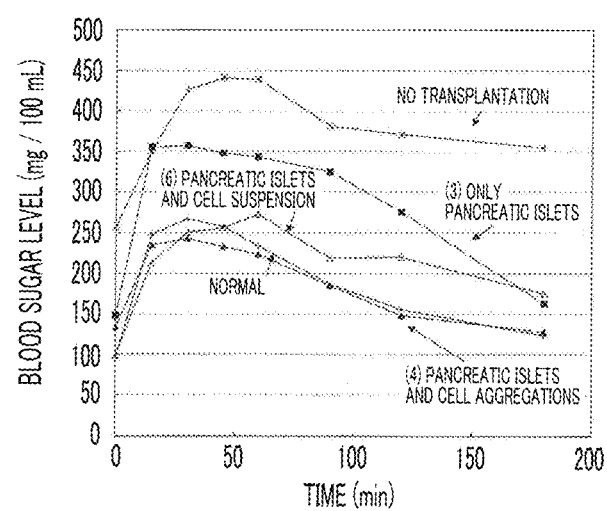
FIG. 8 shows results of glucose tolerance tests of 400 pancreatic islets.

The above-described measurement results are shown in FIGS. 7 and 8. FIG. 7 shows results of (1), (2), and (5) in the case of 200 pancreatic islets and FIG. 8 shows results of (3), (4), and (6) in the case of 400 pancreatic islets.

In the case of 200 pancreatic islets, the area of each lower portion was 45614 min·mg/dl for (1), 43104 min·mg/dl for (2), and 44003 min·mg/dl for (5).

In the case of (1) in which only 200 pancreatic islets were transplanted, although the condition of the blood sugar level was not as high as that of the mouse, into which transplantation was not performed, it resulted that the blood sugar level was hard to decrease. In contrast, in the case of (5) in which a cell suspension and pancreatic islets were transplanted, it resulted that the blood sugar level was not increased compared to the case (1) in which only pancreatic islets were used. Furthermore, in the case of (2) in which a mixture of spheroids and 200 pancreatic islets was transplanted, it resulted that the blood sugar level was more decreased than that of (5).

In the case of 400 pancreatic islets, the area of each lower portion was 51795 min·mg/dl for (3), 32752 min·mg/dl for (4), and 39410 min·mg/dl for (6).

In the case of (3) in which only pancreatic islets were used, although the condition of the blood sugar level was not as high as that of the mouse, into which transplantation was not performed, it resulted that the blood sugar level was hard to decrease. In contrast, in the case of (6) in which a cell suspension and pancreatic islets were transplanted, it resulted that the blood sugar level was not increased compared to the case of (3) in which only pancreatic islets were used. Furthermore, in the case of (4) in which spheroids and pancreatic islets were transplanted, it resulted that the blood sugar level was more decreased than that of (6).

From these results, it was possible to confirm that, in either case of 200 pancreatic islets or 400 pancreatic islets, the case where pancreatic islets and a cell suspension were transplanted or the case where pancreatic islets and hMSC spheroids were transplanted had a high ability to normalize the blood sugar level, compared to the case of only pancreatic islets.

Finally, the results are summarized in Table 3.

TABLE 3

| | In vitro SI | 200 pancreatic islets in vivo | | 400 pancreatic islets in vivo |
| --- | --- | --- | --- | --- |
| | | Blood sugar level (mg/100 dl) on day 28 | AUC (min mg/ 100 dl) in glucose tolerance test | AUC (min mg/ 100 dl) in glucose tolerance test |
| Only pancreatic islets | — | 398 | 45614 | 51795 |
| Pancreatic islets + hMSC spheroids | 2.04 | 183 | 43104 | 32752 |
| Pancreatic islets + hMSC cell suspension | 1.41 | 268 | 44003 | 39410 |

[Sequence Table]

International Application 15F00615 Composition, Cell Structure, and Pancreatic islet transplantation kit JP15-077516 20150929----00110268851501942915 Normal 20-15 092914305420150914180047391O_P1AP101_15_3.app Based on International Patent Cooperation Treaty

What is claimed is:

1. A composition comprising:
   (A): a cell structure which contains a biocompatible macromolecular block and at least one kind of cell and in which a plurality of the macromolecular blocks are arranged in gaps between a plurality of the cells; and
   (B): a pancreatic islet,
   wherein said biocompatible macromolecular block is a polypeptide, and said at least one kind of cell comprises a mesenchymal stem cell, and said pancreatic islet is an aggregate of a α cell, a β cell, a δ cell, a ε cell and a PP cell.

2. The composition according to claim 1, wherein the thickness or the diameter of the cell structure is 100 μm to 3 cm.

3. The composition according to claim 1, wherein the biocompatible macromolecular block is formed of a recombinant peptide.

4. A cell structure comprising:
   a biocompatible macromolecular block;
   at least one kind of cell; and
   a pancreatic islet,
   wherein a plurality of the macromolecular blocks are arranged in gaps between a plurality of the cells,
   wherein said biocompatible macromolecular block is a polypeptide, said at least one kind of cell comprises a mesenchymal stem cell, and said pancreatic islet is an aggregate of a α cell, a β cell, a δ cell, ε cell and a PP cell.

5. The cell structure according to claim 4, wherein SI, which is an amount of insulin during culture in 20 mM glucose medium/amount of insulin during culture in 3 mM glucose medium, is greater than or equal to 3.0.

6. The cell structure according to claim 4, wherein the biocompatible macromolecular block is a recombinant peptide.

7. A pancreatic islet transplantation kit, comprising:
   A): a cell structure which contains a biocompatible macromolecular block and at least one kind of cell and in which a plurality of the macromolecular blocks are arranged in gaps between a plurality of the cells; and
   (B): a pancreatic islet,
   wherein said biocompatible macromolecular block is a polypeptide, and said at least one kind of cell comprises a mesenchymal stem cell, and said pancreatic islet is an aggregate of a α cell, a β cell, a δ cell, a ε cell and a PP cell.

8. The pancreatic islet transplantation kit according to claim 7, wherein the thickness or the diameter of the cell structure is 100 μm to 3 cm.

9. The pancreatic islet transplantation kit according to claim 7, wherein the biocompatible macromolecular block is formed of a recombinant peptide.

* * * * *